(12) United States Patent
Yarkoni et al.

(10) Patent No.: US 9,783,778 B2
(45) Date of Patent: Oct. 10, 2017

(54) DEVICES AND METHODS FOR SELECTING APOPTOSIS-SIGNALING RESISTANT CELLS, AND USES THEREOF

(71) Applicant: Cellect Biotechnology LTD, Kfar Saba (IL)

(72) Inventors: Shai Yarkoni, Kfar Saba (IL); Nadir Askenasy, Tel Aviv (IL)

(73) Assignee: Cellect Biotherapeutics Ltd., Kfar Saba (IL)

( * ) Notice: Subject to any disclaimer, the term of this patent is extended or adjusted under 35 U.S.C. 154(b) by 0 days.

(21) Appl. No.: 14/383,288

(22) PCT Filed: Mar. 5, 2013

(86) PCT No.: PCT/IL2013/000026
§ 371 (c)(1),
(2) Date: Sep. 5, 2014

(87) PCT Pub. No.: WO2013/132477
PCT Pub. Date: Sep. 12, 2013

(65) Prior Publication Data
US 2015/0044182 A1 Feb. 12, 2015

Related U.S. Application Data

(60) Provisional application No. 61/607,033, filed on Mar. 6, 2012.

(51) Int. Cl.
| | | |
|---|---|---|
| *C12N 5/00* | (2006.01) |
| *B01D 15/00* | (2006.01) |
| *A61K 35/12* | (2015.01) |
| *A61K 35/28* | (2015.01) |
| *A61K 35/30* | (2015.01) |
| *A61K 35/51* | (2015.01) |

(52) U.S. Cl.
CPC ............ *C12N 5/0081* (2013.01); *A61K 35/12* (2013.01); *A61K 35/28* (2013.01); *A61K 35/30* (2013.01); *A61K 35/51* (2013.01); *B01D 15/00* (2013.01); *C12N 2501/25* (2013.01); *C12N 2501/599* (2013.01)

(58) Field of Classification Search
CPC ........ A61K 35/12; A61K 35/28; A61K 35/30; A61K 35/51; A61K 38/00; A61K 2039/505; A61K 47/48561; A61K 49/0004; A61K 31/519; A61K 51/088; A61K 51/1021; B01D 15/00; C12N 2501/25; C12N 2501/599; C12N 5/0081; C07K 14/52; C07K 14/715; C07K 16/24; C07K 2317/21
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis et al. | |
| 4,800,159 A | 1/1989 | Mullis et al. | |
| 4,885,234 A | 12/1989 | Zengerle | |
| 4,965,188 A | 10/1990 | Mullis et al. | |
| 4,979,959 A | 12/1990 | Guire | |
| 5,098,842 A | 3/1992 | Nakajima et al. | |
| 5,998,024 A | 12/1999 | Frey et al. | |
| 6,040,182 A | 3/2000 | Septak | |
| 6,472,505 B1 | 10/2002 | Condon et al. | |
| 6,526,984 B1 | 3/2003 | Nilsson et al. | |
| 2003/0044389 A1 | 3/2003 | Brown et al. | |
| 2003/0059400 A1 | 3/2003 | Szalay | |
| 2003/0119185 A1* | 6/2003 | Berenson ............ A61L 27/3804 435/372 |
| 2006/0009623 A1 | 1/2006 | Yao et al. | |
| 2009/0130718 A1 | 5/2009 | Short | |
| 2010/0040583 A1 | 2/2010 | Askenasy | |
| 2010/0040662 A1 | 2/2010 | Cotton et al. | |
| 2010/0209945 A1 | 8/2010 | Chung et al. | |
| 2011/0256581 A1 | 10/2011 | Gregory | |

FOREIGN PATENT DOCUMENTS

| | | |
|---|---|---|
| CN | 102123746 A | 7/2011 |
| JP | 2009538615 A | 11/2009 |
| JP | 2010-227015 A | 10/2010 |
| JP | 2010-227313 A | 10/2010 |
| RU | 2357754 | 7/2005 |
| WO | 9925871 A1 | 5/1999 |

(Continued)

OTHER PUBLICATIONS

Askenasy et al "Induction of tolerance using Fas ligand: a double-edged imnnunomodulator" The American Society of Hematology 105: (4) 1396-1404 (2005).
Askenasy et al "Our perception of Developmental Plasticity Esse Est Percipi (to be is to be Perceived)?" Current Stem Cell Research & Therapy 1:85-94 (2006).
Beaucage et al "Synthetic strategies and parameters involved in the synthesis of oligodeoxyribonucleotides according to the phosphoramidite method." PubMed Commons 3:3.3: 1 (May 2001).
Bhat "Multiple Site-Directed Mutagenesis" Methods in Molecular Biology 57 (24) 269-277 (1996).
Bohana-Kashtan et al "Selective Reduction of Graft-versus-Host Disease-Mediating Human T Cells by Ex Vivo Treatment with soluble Fas Ligand" J. Immunol. 183 (1) 696-705 (Jul. 2009).

(Continued)

*Primary Examiner* — Debbie K Ware
(74) *Attorney, Agent, or Firm* — Browdy and Neimark, PLLC

(57) ABSTRACT

The description discloses a device and a kit adapted for selection of cells that are resistant to receptor-mediated apoptosis and a method for using the device and kit. The device enables negative selection of mature immune cells which induce graft versus host disease (GvHD) out of a heterogeneous cell population which is introduced into the device. The device enables an efficient cell selection in simplified and cheaper setting by an off the shelf product—a solution that currently do not exist. The description further discloses uses for the device.

16 Claims, 32 Drawing Sheets

(56) References Cited

FOREIGN PATENT DOCUMENTS

| WO | 03002761 A1 | 1/2003 |
|---|---|---|
| WO | 03/020320 | 3/2003 |
| WO | 2004/006951 | 1/2004 |
| WO | 2007138597 A2 | 12/2007 |
| WO | 2012011113 A2 | 1/2012 |

OTHER PUBLICATIONS

Caruthers et al "Chemical Synthesis of Deoxyoligonucleotides by the Phosphoramidite Method" Academic Press 230: (154) : 287-313 (1987).
Wingfield et al "Folding and Purification of Insoluble (Inclusin Body) Proteins from *Escherichia coli*" Current Protocols in Protein Science 6.5.1-6.5.27 (1995).
Delagrave et al "Recursive ensemble mutagenesis" Protein Engineering. 6 (3) 327-331 (1993).
Dwivedi et al "Generation of Multiple Mutations in the Same Sequence via the Polymerase Chain Reaction Using a Single Selection Primer" Analytical Biochemistry 221:425-428 (1994).
Georgantas et al "Ex Vivo Soluble Fas Ligand Treatment of Donor Cells to Selectively Reduce Murine Acute Graft Versus Host Disease" Transplantation 82 (4) 471-479 (Aug. 2006).
Gracz et al "A high-throughput platoform for stem cell niche co-cultures and downstream gene expression analysis" nature cell biology. 1-30 (Feb. 2015).
Ishii et al "Sile-Directed Mutagenesis" Methods in Enzymology. 293:53-71 (1998).
Kegler-Ebo et al "Condo casette mutagenesis: a general method to insert or replace individual codons by using universal mutagenic cassettes" Nucleic Acids Research 22 (9) 1593-1599 (1994).
Kim et al. Benchmark "Multiple Site Mutagenesis with High Targeting Efficiency in one cloning Step" Biotechniques 28 (2) 196-198 (2000).
Kunkel et al "Specific cloning of DNA fragments absent from the DNA of a male patent with an X chromosome deletion" Pro. Natl Acad. Sci. 82:4778-4782 (Jul. 1985).
Romaniec et al "Molecular Cloning of Clostridium thermocellum DNA and the Expression of Further Novel Endo-B-1,4-glucanase Genes in *Escherichia coli*" Journal of General Microbiology 133:1297-1307 (1987).
Meetei et al "Generation of Multiple Site-Specific Mutations in a Single Polymerase Chain Reaction Product" Analytical Biochemistry. 264: 288-291 (May 1998).
Chang et al "Solid-Phase Peptide synthesis using mild base cleavage of N^ a-Flouorenylmethyloxycarbonylamino Acid, exemplified by a synthesis of dihydrosomatostatin" Int. J. Peptide Protein Res. 11:246-249 (1978).
Meienhofer "Peptide Synthesis: A Review of the Solid-Phase Method" 45-149 (1973).
Meienhofer "Peptide Synthesis: A Review of the Solid-Phase Method" 150-267 (1973).
Mikaelian et al "A general and fast method to generate multiple site directed mutations" Nucleic Acids Research 20:2:376 (1992).
Morisot et al, Molecular Therapy 13 (1) (May 2006).
Morisot et al, Molecular Therapy 13(1) S132-S133 (May 2006).
Merrifield et al "Solid Phase Peptide Synthesis. I The Synthesis of a Tetrapeptide" 85:2149-2154(Jan. 1963).
Weiner et al "Site-directe mutagenesis of double-stranded DNA by the polymerase chain reaction" Gene 151:119-123 (1994).
Glick. et al "Molecular biotechnology: Principles and applications of recombinant DNA", 2nd edition, ASM Press, Washington D.C. 109-143 Chapter 6 (1998).
Lubke et al The Peptides, vol. 1, Academic Press, New York (1965).
Guan, et al., Abstract only, Long effect of immobilized IFN-gamma and TNF-alpha on apoptosis of HeLa cells, Huanan Shifan Daxue Xuebao, 2007, pp. 114-118, vol. 2.
Rana, et al., Delivery of Apoptotic Signal to Rolling Cancer Cells: A Novel Biomimetic Technique Using Immobilized TRAIL and E-Selectrin, Biotechnology and Bioengineering, Apr. 15, 2009, pp. 1692-1702, vol. 102, No. 6.
Sashchenko et al., Cytotoxic T lymphocytes carrying a pattern recognition protein Tag7 can detect evasive, HLA-negative but Hsp70-exposing tumor cells, thereby ensuring FASL/Fas-mediated contact killing, Blood, 110(6):1997-2004 (2007).
Sawal et al., Transfer of Fas (CD95) protein from the cell surface to the surface of polystyrene beads coated with anti-Fas antibody clone CH-11, European Journal of Histochemistry, 54(e8):39-43 (2010).
Pearl-Yafe et al., Fas ligand enhances hematopoietic cell engraftment through abrogation of alloimmune responses and nonimmunogenic interactions, Stem Cells, 25:1448-1455 (2007).
Hartwig et al., Murine acute graft-versus-host disease can be prevented by depletion of alloreactive T lymphcytes using activation-induced cell death, Blood, 99(8):3041-3043 (2002).
Pearl-Yafe et al., Fas ligand enhances hematopoietic cell engraftment through abrogation of alloimmune responses and nonimmunogenic interactions, Stem Cells 25:1448-1455 2007). 10.1634/stemcells.2007-003 AlphaMed Press (Mar. 15, 2007).
Sashcehnko et al., Cytotoxic T lymphocytes carrying a pattern recognition protein Tag7 can detect evasive, HLA-negative but Hsp70-exposing tumor cells, thereby ensuring FsdL/Fas-mediated contact killing, Blood, 110 (6):1997-2004 (2007).
Sawai et al., Transfer of Fas (CD95) protein from the cell surfaceto the surface of polystyrene beads coasted with anti-Fas antibody clone CH-11, European Journal of Histochemistry, 54:e8:39-43 (2010).
Scholz et al., Fas/FasL interaction: A novel immune therapy approach with immobilized biologicals, Wiley Periodicals, Inc., Medicinal Research Reviews (2004) (Abstract).
Online publication for Comprised of-Composed Of, downloaded Apr. 5, 2016, from httpspublic.wsu.edu~brainserrorscomprised.html.pdf.
Askenasy et al., Depletion of Naïve Lymphocytes with Fas Ligand Ex Vivo Prevents Graft-versus-Host Disease without Impairing T Cell Support of Engraftment or Graft-versus-Tumor Activity, Biol Blood Marrow Transplant, 19:185-195 (2013).

* cited by examiner

Fig. 15A
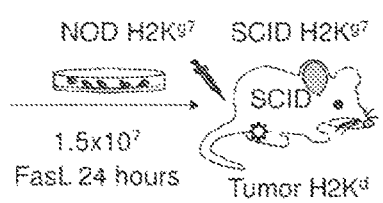
Fig. 15B
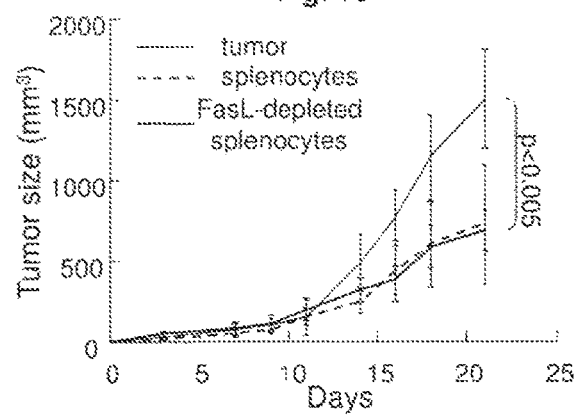
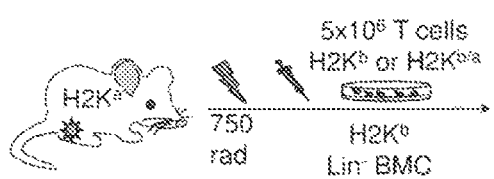
Fig. 15C
Fig. 15D
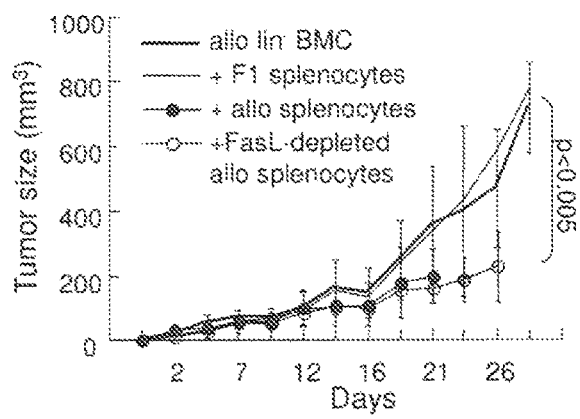

SEQUENCE LISTING

```
<160> NUMBER OF SEQ ID NOS: 4

<210> SEQ ID NO 1
<211> LENGTH: 280
<212> TYPE: PRT
<213> ORGANISM: Homo sapiens

<400> SEQUENCE: 1

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro
        35                  40                  45
```

```
Pro Pro Pro Pro Leu Pro Pro Pro Pro Pro Pro Leu Pro
    50              55                  60
Pro Leu Pro Leu Pro Pro Leu Lys Lys Arg Gly Asn His Ser Thr Gly
65              70                  75                  80
Leu Cys Leu Leu Val Met Phe Phe Met Val Leu Val Ala Leu Val Gly
                    85                  90                  95
Leu Gly Leu Gly Met Phe Gln Leu Phe His Leu Gln Lys Glu Leu Ala
                100                 105                 110
Glu Leu Arg Glu Ser Thr Ser Gln Met His Thr Ala Ser Ser Leu Glu
            115                 120                 125
Lys Gln Ile Gly His Pro Ser Pro Pro Glu Lys Lys Glu Leu Arg
        130                 135                 140
Lys Val Ala His Leu Thr Gly Lys Ser Asn Ser Arg Ser Met Pro Leu
145                 150                 155                 160
Glu Trp Glu Asp Thr Tyr Gly Ile Val Leu Leu Ser Gly Val Lys Tyr
                165                 170                 175
Lys Lys Gly Gly Leu Val Ile Asn Glu Thr Gly Leu Tyr Phe Val Tyr
                180                 185                 190
Ser Lys Val Tyr Phe Arg Gly Gln Ser Cys Asn Asn Leu Pro Leu Ser
            195                 200                 205
His Lys Val Tyr Met Arg Asn Ser Lys Tyr Pro Gln Asp Leu Val Met
        210                 215                 220
Met Glu Gly Lys Met Met Ser Tyr Cys Thr Thr Gly Gln Met Trp Ala
225                 230                 235                 240
Arg Ser Ser Tyr Leu Gly Ala Val Phe Asn Leu Thr Ser Ala Asp His
                245                 250                 255
Leu Tyr Val Asn Val Ser Glu Leu Ser Leu Val Asn Phe Glu Glu Ser
                260                 265                 270
Gln Thr Phe Phe Gly Leu Tyr Lys
            275                 280

<210> SEQ ID NO 2
<211> LENGTH: 233
<212> TYPE: PRT
<213> ORGANISM: Homo sapiens

<400> SEQUENCE: 2

Met Ser Thr Glu Ser Met Ile Arg Asp Val Glu Leu Ala Glu Glu Ala
1               5                   10                  15
Leu Pro Lys Lys Thr Gly Gly Pro Gln Gly Ser Arg Arg Cys Leu Phe
                20                  25                  30
Leu Ser Leu Phe Ser Phe Leu Ile Val Ala Gly Ala Thr Thr Leu Phe
            35                  40                  45
Cys Leu Leu His Phe Gly Val Ile Gly Pro Gln Arg Glu Glu Phe Pro
        50                  55                  60
Arg Asp Leu Ser Leu Ile Ser Pro Leu Ala Gln Ala Val Arg Ser Ser
65                  70                  75                  80
Ser Arg Thr Pro Ser Asp Lys Pro Val Ala His Val Val Ala Asn Pro
                85                  90                  95
Gln Ala Glu Gly Gln Leu Gln Trp Leu Asn Arg Arg Ala Asn Ala Leu
                100                 105                 110
Leu Ala Asn Gly Val Glu Leu Arg Asp Asn Gln Leu Val Val Pro Ser
            115                 120                 125
Glu Gly Leu Tyr Leu Ile Tyr Ser Gln Val Leu Phe Lys Gly Gln Gly
```

-continued

```
                130                 135                 140
Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
                195                 200                 205

Ser Ala Glu Ile Asn Arg Pro Asp Tyr Leu Asp Phe Ala Glu Ser Gly
                210                 215                 220

Gln Val Tyr Phe Gly Ile Ile Ala Leu
225                 230
```

<210> SEQ ID NO 3
<211> LENGTH: 280
<212> TYPE: PRT
<213> ORGANISM: Homo sapiens

<400> SEQUENCE: 3

```
Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Met Gln Asp Lys
                35                  40                  45

Tyr Ser Lys Ser Gly Ile Ala Cys Phe Leu Lys Glu Asp Asp Ser Tyr
50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
                100                 105                 110

Leu Val Arg Glu Arg Gly Pro Gln Arg Val Ala Ala His Ile Thr Gly
                115                 120                 125

Thr Arg Gly Arg Ser Asn Thr Leu Ser Ser Pro Asn Ser Lys Asn Glu
                130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
                180                 185                 190

Gln Glu Glu Ile Lys Glu Asn Thr Lys Asn Asp Lys Gln Met Val Gln
                195                 200                 205

Tyr Ile Tyr Lys Tyr Thr Ser Tyr Pro Asp Pro Ile Leu Leu Met Lys
                210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
                260                 265                 270
```

-continued

```
Ser Phe Phe Gly Ala Phe Leu Val
        275                 280

<210> SEQ ID NO 4
<211> LENGTH: 249
<212> TYPE: PRT
<213> ORGANISM: Homo sapiens

<400> SEQUENCE: 4

Met Ala Ala Arg Arg Ser Gln Arg Arg Gly Arg Arg Gly Glu Pro
1               5                   10                  15

Gly Thr Ala Leu Leu Val Pro Leu Ala Leu Gly Leu Gly Leu Ala Leu
                20                  25                  30

Ala Cys Leu Gly Leu Leu Leu Ala Val Val Ser Leu Gly Ser Arg Ala
            35                  40                  45

Ser Leu Ser Ala Gln Glu Pro Ala Gln Glu Glu Leu Val Ala Glu Glu
        50                  55                  60

Asp Gln Asp Pro Ser Glu Leu Asn Pro Gln Thr Glu Glu Ser Gln Asp
65                  70                  75                  80

Pro Ala Pro Phe Leu Asn Arg Leu Val Arg Pro Arg Arg Ser Ala Pro
                85                  90                  95

Lys Gly Arg Lys Thr Arg Ala Arg Arg Ala Ile Ala Ala His Tyr Glu
                100                 105                 110

Val His Pro Arg Pro Gly Gln Asp Gly Ala Gln Ala Gly Val Asp Gly
            115                 120                 125

Thr Val Ser Gly Trp Glu Glu Ala Arg Ile Asn Ser Ser Ser Pro Leu
        130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asp Gly Val Leu Ala Leu Arg Cys Leu
                180                 185                 190

Glu Glu Phe Ser Ala Thr Ala Ala Ser Ser Leu Gly Pro Gln Leu Arg
            195                 200                 205

Leu Cys Gln Val Ser Gly Leu Leu Ala Leu Arg Pro Gly Ser Ser Leu
        210                 215                 220

Arg Ile Arg Thr Leu Pro Trp Ala His Leu Lys Ala Ala Pro Phe Leu
225                 230                 235                 240

Thr Tyr Phe Gly Leu Phe Gln Val His
                245
```

DEVICES AND METHODS FOR SELECTING APOPTOSIS-SIGNALING RESISTANT CELLS, AND USES THEREOF

A Sequence Listing in ASCII text file format of 9546 bytes in size, created on Sep. 5, 2017, with the file name "2017-09-05SequenceListing_YARKONI4" is incorporated herein by reference.

FIELD OF THE INVENTION

The present invention relates to the field of medical devices and more specifically, to devices aimed at selecting cells that are resistant to apoptosis signaling, methods of using the devices and uses thereof.

BACKGROUND OF THE INVENTION

Stem cells are cells that can both divide and differentiate into diverse specialized cell types and self-renew to produce more stem cells. In mammals, stem cells are found as either embryonic stem cells, which are isolated from the inner cell mass of blastocysts, or adult stem cells, which are found in various tissues. In adult organisms, stem cells and progenitor cells act as a repair system for the body, replenishing adult tissues.

Unlike all current treatments relying upon surgical intervention or drugs that modulate physiological activities, stem cells provide a replacement for dysfunctional or degenerating tissue. Therefore, the use of stem cells in replacement therapy could dramatically change the prognosis of many currently untreatable diseases, restore function of damaged organs and correct inborn disorders of metabolism and deficiencies. The importance of technologies associated with expansion of stem cells, both of adult and/or embryonic derivation is illustrated by the numerous preclinical and clinical uses of these cells in treatment of a wide range of diseases.

More recent developments have shown that several stem cells within the hematopoietic compartment, including hematopoietic stem and progenitor cells (HSPC) and mesenchymal stromal cells (MSC) have the capacity to differentiate into cell types outside the immuno-hematopoietic system, creating an opportunity to use these cell types for tissue repair and regeneration in a wide spectrum of degenerative disorders, end organ failure and dysfunction, and possibly replace organ transplants by cellular therapies.

One of the major clinical uses of stem cells is via hematopoietic stem cell transplants (HSCT). In this procedure a number of cells from a donor are transferred to a recipient in aim of reconstituting the recipient's immune and hematopoietic systems. While performing these transplants, it was realized that immune reconstitution is in fact the best therapy for a number of chemotherapy-resistant cancers such as leukemia, lymphoma, multiple myeloma and a number of solid tumors. Beyond its use in oncology, HSCT harbors the potential of curing non-malignant disorders, such as autoimmune diseases (e.g. Diabetes T1, SLE, and Crohns' disease), inborn errors of metabolism and enzyme deficits, hemoglobinopathies or congenital and acquired immunodeficiency. HSCT has been used for non-cancer indications, showing significant positive results. Nevertheless, this procedure is currently employed for life threatening conditions because of its severe toxicity effects of which Graft versus host disease (GvHD) is the most critical.

When using this approach for the treatment of cancer, it was most frequently performed following myeloablative preconditioning by eradication of the immuno-hematopoietic system through aggressive radio-chemotherapy so as to prevent graft rejection. The recent realization that a hosts's immuno-hematopoietic system does not need to be eradicated prior to grafting had been a significant advancement, thus replacing myeloablative preconditioning with non-myeloablative preconditioning and reduced intensity conditioning (RIC). The use of non-myeloablative preconditioning has improved significantly, yet not sufficiently, life-threatening situations caused by vital organ dysfunction, failure of engraftment and intractable infections. Since host's hematopoietic system is not eradicated by RIC, it can recover in case the donor cells fail to engraft. With time, the donor graft takes over, a process that facilitates the generation of graft versus tumor (GvT) and graft versus autoimmunity (GvA) reactions, yet further expose the patient to GvHD critical morbidity and mortality.

The identification of the type 1 transmembrane protein/adhesion molecule, the sialomucin CD34 as a marker of hematopoietic stem cells led to the ability to use CD34+ cell selection as a means of concentrating hematopoietic stem cells for transplantation purposes. CD34 markers is absent from some stem cells and found also on various subtypes of blood precursors. Using such a positive selection method results in loss of some of the beneficial stem cells. Moreover, it yields a mixed cell population of stem and progenitor cells with some later precursor cells. Transplantation of such a mixed cell population decreases transplantation success [Askenasy N. et al., Current Stem Cell Research and Therapy 2006; 1:85-94]. Therefore, a need arose for a selection method which retains all the cells needed for hematopoietic reconstitution while discarding the adverse effects causing cells.

Unlike somatic cells, hematopoietic stem and progenitor cells (HSPC), mesenchymal stromal cells and neural progenitors (NP) have been documented to be insensitive to injury factors such as those inflicted both by radio-chemotherapy and by secondary factors released into the marrow space as a result of massive death of resident hematopoietic cells. HSPC are particularly resistant to apoptotic signals transduced by tumor necrosis factor (TNF) family receptors, which are instead utilized to deliver growth signals in the most primitive progenitors. In murine models, hematopoietic progenitors have been shown to acutely upregulate several TNF family receptors under conditions of injury and stress. In the transplant setting, this physiological mechanism prioritizes more primitive progenitors for engraftment over apoptosis-sensitive donor cells. Therefore, exposure of a transplant population to TNF family apoptosis-inducing ligands such as FasL, Trail, Tweak or TNF-α results in negatively selecting the stem cell population, as cell populations sensitive for TNF-family ligand induced apoptosis undergo apoptosis and are removed from the transplant. The use of such method in a murine model has been disclosed in patent application WO 2007/138597.

The composition of the donor graft is a significant parameter of stem cell transplant. It has been shown that a threshold number of progenitors is required in order to ensure engraftment. In addition, the presence of some non-stem cell subsets substantially improves the probability of engraftment, such that the transplantation of heterogeneous mixtures of cells is more effective than transplantation of purified progenitors. The most significant subsets within the donor graft are (CD4$^+$ and CD8$^+$) T cells as they have been demonstrated to counteract rejection and support hematopoietic progenitor engraftment within the bone marrow microenvironment. However, transplantation of allogeneic T cells into partially immunosuppressed recipients supports durable engraftment, which mediates a potentially lethal graft versus host reaction (GvH) or graft versus host disease (GvHD). Mature donor T cells mediate this reaction, whereas donor T cells that develop de novo after transplantation are tolerant to the host. Extensive efforts have been invested in dissociation between T cell subsets that mediate GvH and support engraftment; however the experimental evidence has been so far inconclusive.

Graft versus host disease (GvHD) includes an acute phase reaction, usually within the first 100 days post-transplantation, and a chronic reaction with more indolent progression but equally detrimental consequences. Importantly, both reactions are triggered by initial inflammation mediated by mature donor T cells within days from transplantation. Acute GvHD is usually treated by immunosuppressive therapy, which has negative effects on hematopoietic reconstitution, whereas there is no current effective therapy for the chronic reaction. The traditional approach to prevention of GvHD consists of depletion of mature T cells from the donor inoculum, at times accompanied by B lymphocytes, using cell surface makers such as CD3, CD4, CD8. Intensive efforts to achieve more selective T cell depletion (TCD) using various cell surface markers have failed.

More specific depletion has been achieved with decent results by elimination of reactive T cell subsets using apoptotic signals following ex vivo sensitization against host antigens. Sensitized T cells express repertoires of activation-related molecules, become sensitive to activation-induced cell death (AICD) and proliferate at fast rates, characteristics that are used for specific depletion. However, there are several major hurdles to this approach to selective elimination. First, sensitization of T cells is a process of repeated exposure to antigens, which requires 3-7 days of ex vivo incubation. Consequently, T cell activation has to be performed at least 3 days prior to transplantation. Second, sensitization and activation that render fast-cycling T cells susceptible to AICD, also induces the development and expansion of effector/memory T cells, whose persistent alloreactivity can initiate and propagate GvHD. Effector/memory T cells are relatively resistant to Fas cross-linking, in part due to inherent low levels of caspase-3, resulting in an apoptosis-resistant phenotype that predisposes patients to acute and chronic GvHD after infusion of the ex vivo cultured T cells. Third, the most effective ex vivo sensitization is against components of the major histocompatibility complex (MHC), the disparity of which leads to dominant alloresponses in the transplant setting. However, the GvHD reaction is stimulated primarily by minor histocompatibility complex antigens (miHA) and targets mainly tissue-specific antigens (TSA). Normal and aberrant tissue epitopes are exposed by injury inflicted by pre-transplant conditioning and by inflammation. An effective method for selective depletion of T cells which induce GvHD, while retaining subsets of cells which support GvT and transplant engraftment, is yet to be found.

SUMMARY OF THE INVENTION

The present invention discloses a device and a kit adapted for selection of cells that are resistant to receptor-mediated apoptosis and a method for using the device and kit. The device enables simultaneous positive selection for both stem-cells and immune cells which support engraftment and negative selection for immune cells which induce graft versus host disease (GvHD) out of a heterogeneous cell population which is introduced into the device. The device can enable single step cell selection in simplified setting by an off the shelf product, a solution that currently do not exist. The present invention further discloses uses for the device.

According to one aspect, the present invention discloses a device, comprising a container which is made of a biocompatible material and a biologically active apoptosis-inducing ligand immobilized to a surface, wherein the device is adapted for cell selection.

According to one embodiment, the surface to which the biologically active apoptosis-inducing ligand is immobilized is the inner surface of the container.

According to another embodiment, the surface to which the biologically active apoptosis-inducing ligand is immobilized is the surface of beads present within the container.

According to another embodiment, the container is selected from the group comprising a bag, a column, a tube, a bottle, a vial and a flask.

According to yet another embodiment, the biocompatible material from which the device is comprised is selected from the group comprising: polypropylene, polystyrene, silicone, polyvinyl chloride or a combination thereof.

According to yet another embodiment, the immobilized apoptosis-inducing ligand is selected from a group comprising: tumor necrosis factor α (TNF-α), Fas ligand (FasL), Trail, Tweak, or any combination thereof.

According to another aspect, the present invention discloses a method for selecting an apoptosis-signaling resistant cell from a heterogeneous cell population; the cell population comprises apoptosis-signaling resistant cells and apoptosis-signaling sensitive cells. The method consists of introducing a sample, comprising a heterogeneous cell population, into the device of the present invention and incubating the cells within the device, thereby selecting apoptosis-signaling resistant cells from the cell population.

According to another embodiment, the selected apoptosis-resistant cell is a stem cell, selected from a group comprising: umbilical cord blood stem cell, mobilized peripheral blood stem cell, bone marrow stem cell, cancer stem cell, and neural stem cell.

According to another embodiment, the selected apoptosis-resistant cell is an immune cell insensitive to activation-induced cell death (AICD). In yet another embodiment, the immune cell insensitive to activation-induced cell death (AICD) is a T cell.

According to another embodiment, the selected apoptosis-resistant cell is a progenitor cell.

According to yet another embodiment, the cell population used in the method is derived from: bone marrow, a progenitor cell mobilized peripheral blood, or umbilical cord blood (UCB).

According to yet another embodiment, the incubation time within the device is from 2 hours to 72 hours.

According to yet another aspect, the present invention discloses a cell selection kit comprising the device of the invention and a solution for maintaining the integrity and activity of an apoptosis-inducing ligand within the device. In some embodiments, the kit further comprises an apoptosis inducing ligand, selected from the group of tumor necrosis factor α (TNF-α), Fas ligand (FasL), Trail, Tweak, or any combination thereof.

According to another embodiment, the solution for maintaining the integrity and activity of an apoptosis-inducing ligand is a buffer or media.

According to yet another aspect, the present invention discloses a method of use for the abovementioned device and method. The method is a method for improving the clinical outcome of hematopoietic stem and progenitor cells (HSPC) transplantation. In the method, a sample comprising a cell population is provided; the cell population comprises stem and progenitor cells. The population is contacted with an apoptosis-inducing ligand, and the remaining cells are retrieved and used for transplantation. According to a further embodiment, the contacting occurs within the device of the present invention.

According to another embodiment, the cell population in the method is derived from: bone marrow, a progenitor cell mobilized peripheral blood, or umbilical cord blood (UCB).

According to another embodiment, the stem cell which is selected using the method, is selected from a group comprising: umbilical cord blood stem cell, mobilized peripheral blood stem cell, bone marrow stem cell, cancer stem cell, and neural stem cell.

According to another embodiment, the population of cell is incubated with Fas Ligand (FasL) for a period of 21 to 24 hours and with tumor necrosis factor α (TNF-α) for a period of 24 to 48 hours.

According to another embodiment, retrieved cells from the method are used for either autologous, allogeneic or haploidentical transplants.

According to another embodiment, the retrieved cells in the method further comprise an immune-cell insensitive to activation-induced cell death (AICD). In yet another embodiment, the immune cell insensitive to activation-induced cell death (AICD) is a T cell.

According to yet another aspect, the present invention discloses another method of use for the abovementioned device and method. The method is a method for eliminating a malignant cell in a composition comprising a progenitor-cell transplant. In the method a composition comprising a progenitor-cell transplant is provided and then contacted with an apoptosis-inducing ligand. According to a further embodiment, the contacting occurs within the device of the present invention.

According to another embodiment, the composition is contacted with the apoptosis-inducing ligand Fas Ligand (FasL) for a period of about 24 hours.

According to another embodiment, the progenitor-cell transplant is used as an autologous transplant.

According to another aspect, the present invention discloses yet another method of use for the abovementioned device and method. The method is a method for preventing graft vs. host disease (GvHD) while retaining graft vs. tumor (GvT) activity. In the method, a sample comprising a cell population is provided, the cell population comprises HSPC and immune cells. The population is contacted with an apoptosis-inducing ligand, and the remaining cells are retrieved and used for transplantation. According to a further embodiment, the contacting occurs within the device of the present invention.

According to another embodiment, the composition is contacted with the apoptosis-inducing ligand Fas Ligand (FasL) for a period of 2-16 hours.

Further embodiments, features, advantages and the full scope of applicability of the present invention will become apparent from the detailed description and drawings given hereinafter. However, it should be noted that the detailed description, while indicating preferred embodiments of the invention, is given by way of illustration only, since various changes and modifications within the spirit and scope of the invention will become apparent to those skilled in the art from this detailed description.

BRIEF DESCRIPTION OF FIGURES

FIG. 2.

FIG. 3.

FIG. 4.

FIG. 5.

FIG. 6.

FIG. 8.

FIG. 9.

FIG. 10.

FIG. 11.

FIG. 13.

FIG. 14.

FIG. 15. FIGS. 15A, 15C, 15E and 15G are schemes and FIGS. 15B, 15D, 15F and 15H are graphs showing that transplantation of FasL-depleted unstimulated lymphocytes retains graft versus host activity. (A) NOD.SCID mice (H2K$^{g7}$) bearing subcutaneous allogeneic (H2K$^d$) CT26 colon carcinoma tumors were infused (1 day after tumor implantation) with 1.5×10$^7$ splenocytes from 5 weeks old host-matched NOD donors (H2K$^{g7}$). (B) Infusion of lymphocytes suppressed tumor growth in NOD.SCID mice (n=10) irrespective of preincubation for 24 hours in medium and with FasL (n-8). (C) H2K$^a$ mice bearing MHC-matched subcutaneous neuroblastoma (Neuro-2a, H2K$^a$) tumors were sublethally irradiated (750 rad) and grafted with 2×10$^6$ lineage-negative bone marrow cells from allogeneic donors (H2K$^b$). (D) Infusion of lymphocytes from F1 donors (H2K$^{b/d}$), devoid of GVH activity, had no significant impact on tumor growth (n=17). Infusion of allogeneic splenocytes (H2K$^b$) incubated in medium for 24 hours reduced tumor growth rates (n=10), but 80% of the mice died within 3 weeks because of severe GvHD. Infusion of splenocytes preincubated with FasL equally reduced tumor growth but all mice were alive (n=1). (E) Sublethally irradiated (750 rad) BALB/c mice were infused with a mixture of 5×10$^6$ syngeneic (H2K$^d$) bone marrow cells and 2×10$^5$ A20 Lymphoblastoma cells (H2K$^d$). The cell mixtures were preincubated for 24 hours in medium and with FasL. (F) Recipients of bone marrow and A20 cells incubated in medium developed disseminated tumors with lethal outcome (n=10), whereas recipients of cells preincubated with FasL survived (n=10). (G) Immunocompromized NOD.SCID mice (H2K$^{g7}$) irradiated at 650 rad were adoptively transferred with 5×10$^7$ bone marrow cells from syngeneic NOD donors (H2K$^{g7}$) after 48 hours of incubation in medium and with 50 ng/ml FasL protein. Hyperglycemia was considered following two measurements of fasting blood glucose levels exceeding 200 mg/dl. (H) Development of hyperglycemia after adoptive transfer of whole bone marrow cells preincubated in medium and with FasL protein (n=10).

DETAILED DESCRIPTION OF THE INVENTION

Figure 1A:
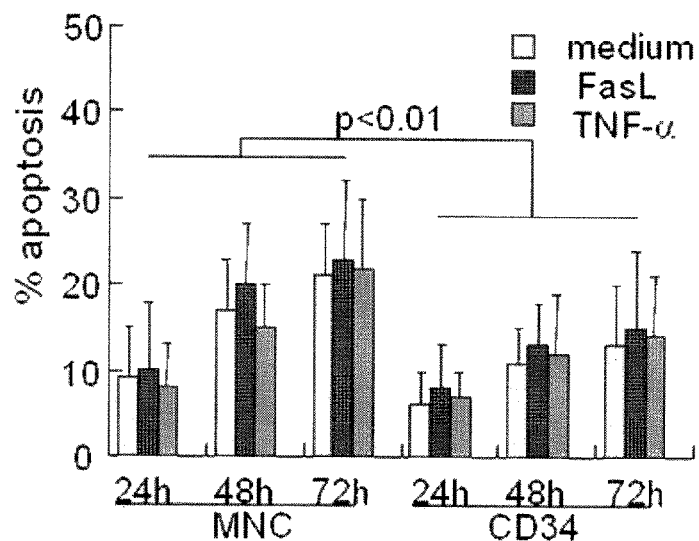
FIG. 1. A set of graphs showing the sensitivity of UCB cells to receptor-mediated apoptosis in vitro. (A) Fresh samples of UCB cells were incubated in medium without chemokine supplements for variable periods of time (n=35) and were exposed to 50 ng/ml FasL oligomers (n=21) and 20 ng/ml TNF-alpha (n=18). Apoptosis was determined from Annexin-V uptake in mononuclear cells (MNC) and gated CD34+ progenitors. (B) Expression of the Fas and TNF receptors in fresh UCB mononuclear cells, gated CD34+ and isolated lineage-negative (lin−) progenitors. (C) Apoptosis was measured as a function of time in gated CD34+ progenitors expressing Fas and the TNF receptors under the influence of the cognate ligands (n=15-21). (D) Proliferation rates in MNC and gated CD34+ progenitors expressing Fas and the TNF receptors incubated with the cognate ligands (n=6). Proliferation was measured from CFSE dilution using the ModFit software. (E) Expression of Fas and TNF receptors in T cells (CD3+), B lymphocytes (CD19+) and myeloid cells (CD33+) in fresh UCB samples (n=8-13). (F) Apoptosis as determined from Annexin-V uptake in lineage-positive UCB subsets, including monocytes/macrophages (CD14+), exposed for 48 hours to FasL and TNF-□ (n=6-14).

In one embodiment, the present invention discloses a device for selecting an apoptosis-signaling resistant cell. In another embodiment, apoptosis-signaling resistant cell is selected from the group comprising: stem-cell, progenitor cell and an immune cell. In another embodiment, immune cells of the invention are a subset of T-cells. In another embodiment, a cell of the invention is a hematopoietic cell. In another embodiment, a cell of the invention is identified on the basis of a surface phenotype, e.g. CD34+. In another embodiment, apoptosis-signaling resistant cell is a cell of the invention.

In another embodiment, apoptosis-signaling resistant cell is resistant to TNF-alpha. In another embodiment, apoptosis-signaling resistant cell is resistant to Fas ligand. In another embodiment, apoptosis-signaling resistant cell is resistant to TRAIL. In another embodiment, apoptosis-signaling resistant cell is resistant to Tweak. In another embodiment, apoptosis-signaling resistant cell is resistant to TNF-alpha, Fas ligand, TRAIL, Tweak, or any combination thereof.

In another embodiment, the present invention provides methods and devices that overcome the hurdles and inaccuracies associated with methods of cell staining for the identification of stem cell or "stemness". In another embodiment, the prior art typically provides methods for the identification of a stem cell wherein the present invention provides means for selecting a stem cell from a culture, wherein the culture comprises various cell types including non-stem cells. In another embodiment, selection is performed in one step.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

In another embodiment, the device of the present invention comprises a container, with an apoptosis-inducing ligand immobilized to the inner surface of the container. In another embodiment, the device of the present invention comprises a container, with an apoptosis-inducing ligand immobilized to the surface of beads introduced therein. In another embodiment, the device of the present invention comprises a container, with an apoptosis-inducing ligand immobilized to the surface of beads contained within the device. In another embodiment, the device of the present invention is utilized for selecting stem-cells using a single step. In another embodiment, single step includes the incubation of a heterogeneous cell population within the container. In another embodiment, incubation exposes the cell population to apoptotic ligands as provided herein. In another embodiment, incubation results in survival of apoptotic-resistant cells such as stem-cells and apoptotic death of apoptosis-sensitive cell types.

In another embodiment, a selected population of apoptotic-resistant cells (such as stem cells) is used for transplanting in the course of treating a disease, such as, but not limited to: cancer, immune diseases, chemotherapy-resistant cancer, or congenital or acquired immunodeficiency. In another embodiment, one of skill in the art can readily determine the use of apoptosis resistant cells of the invention.

In another embodiment, the container is constructed of at least one biocompatible material. In another embodiment, a biocompatible material includes but not limited to: polypropylene, polystyrene, silicone, polyvinyl chloride or a combination thereof. In another embodiment, a biocompatible material is selected according to parameters such as, but not limited to: durability or ability to facilitate immobilization of apoptosis-inducing ligands on its inner surface or transparency. In another embodiment, a biocompatible material is inert with respect to eliciting any undesirable local or systemic effects in the recipient or beneficiary of that therapy, but generating the most appropriate beneficial cellular or tissue response in that specific situation, and optimizing the clinically relevant performance of that therapy (Biocompatible materials are exemplified by U.S. Pat. No. 5,998,024, U.S. Pat. No. 6,526,984 and U.S. Pat. No. 4,979,959). In another embodiment, a biocompatible material comprises a hydrophobic polymer coated with at least one layer that promotes the survival of apoptosis resistant cells of the invention.

In another embodiment, the container is a bag. In another embodiment, the container is a column. In another embodiment, the container is a tube. In another embodiment, the container is a bottle. In another embodiment, the container is a vial. In another embodiment, the container is a flask. In another embodiment, the container is any other receptacle which is known in the art and suits the specific intended use of the device.

According to one embodiment, the device is comprised of a single container into which a cell-population is introduced. In another embodiment, the container comprises two interlocking chambers separated by a filter apparatus adapted to separate whole cells from cell debris and proteins. In another embodiment, a cell-population is introduced into one chamber, incubated within the chamber and after incubation the filter may be used to further isolate the selected cells from cell debris and proteins in the solution.

According to another embodiment, the container is in the form of a column in which the cell population is incubated, allowing attachment of whole cells, or specifically of stem cells, to the column. In another embodiment, following incubation, the remaining cell debris and proteins are discarded and the selected cells are isolated from the column. The use of such a column has been exemplified in U.S. Pat. No. 5,098,842 and in patent application US 2011/0256581.

In another embodiment, members of the Tumor Necrosis Factor (TNF) family are used as apoptotic inducing agents for selecting an apoptosis resistant cell. In another embodiment, a TNF-family apoptosis-inducing ligand that is used in accordance with the present invention is: TNF-α, FasL, Trail (Apo2 ligand) or Tweak (Apo3 ligand). In another embodiment, a pro-apoptotic agent is a recombinant protein.

In another embodiment, a biologically active apoptosis inducing ligand is a ligand that is active in its apoptosis inducing activity while immobilized to an inner surface of a container. In another embodiment, a biologically active apoptosis inducing ligand is any of: TNF-α, FasL, Trail and Tweak comprising at least an active portion capable of binding the respective receptors and inducing apoptosis in its immobilized form.

In another embodiment, an apoptosis inducing ligand is derived from a mammalian source. In another embodiment, an apoptosis inducing ligand is a human apoptosis inducing ligand. In another embodiment, an apoptosis inducing ligand is a rodent apoptosis inducing ligand.

According to another embodiment, the biologically active apoptosis-inducing ligands are immobilized to the inner surface of the container. In another embodiment, the biologically active apoptosis-inducing ligands are immobilized to beads within the container. In another embodiment, the biologically active apoptosis-inducing ligands are immobilized in a manner that allows free interaction of the ligands with cells contained within the container.

There are many methods known in the art for immobilizing a protein to a surface. Most immobilization methods involve modification or coating of the surface with appropriate substances to change the surface property or provide functional groups for the binding of protein. On the other hand, immobilization of proteins on a bare surface with no modification necessitates using an affinity peptide that is specific to the particular surface. In another embodiment, immobilization is achieved by utilizing a chelator compatible with the apoptosis inducing ligand of the invention. In another embodiment, one of skill in the art can readily identify the proper chelator. In another embodiment, a chelator is both compatible with the apoptosis inducing ligand of the invention and maintains its biological activity. In another embodiment, a chelator is both compatible with the apoptosis inducing ligand of the invention and promotes its biological activity.

In another embodiment, immobilization of an apoptosis-inducing ligand is achieved by: physical adsorption, interaction between His-6 and Ni$^+$ ions, coiled coil association of a heterodimeric Leu zipper pair, Chemisorption of SH-groups, Schiff's base linkage between aldehyde and amino groups, acyl transfer reaction of TGase, affinity between streptavidin-biotin, affinity between FLAG and anti-FLAG antibody, affinity between glutathione and GST or binding of a protein fused with a PS-affinity peptide to hydrophilic polystyrene (various methods for immobilization are exemplified in U.S. Pat. No. 6,040,182, U.S. Pat. No. 4,885,234, patent application US 2010/0209945 and patent application US 2006/0009623).

In another embodiment, an apoptosis inducing ligand is a derivative or an analogue of the full protein. In another embodiment, an apoptosis inducing ligand is a small organic molecule. In another embodiment, an apoptosis inducing ligand is a variant, derivative, modified version or truncated version of the full protein. In another embodiment, FasL is a human FasL such as set forth in SEQ ID NO: 1. In another embodiment human TNF-α of the invention comprises SEQ ID NO: 2. In another embodiment human Trail of the invention comprises SEQ ID NO: 3. In another embodiment human Tweak of the invention comprises SEQ ID NO: 4.

The proteins disclosed herein may be produced by recombinant or chemical synthetic methods.

In another embodiment, provided herein a method for selecting apoptosis-resistant cells out of a heterogeneous cell population, wherein the heterogeneous population comprises apoptosis-signaling resistant cells and apoptosis-signaling sensitive cells. In another embodiment, the method consists of introducing the heterogeneous cell population into the device and incubation therein. In another embodiment, the method comprises of introducing the heterogeneous cell population into the device and incubation therein.

In another embodiment, the term "selecting" as used herein refers to a method in which only a selected cell out of a heterogeneous cell population survives. In another embodiment, the surviving cell is an apoptosis-signaling resistant cell.

In another embodiment, an apoptosis-signaling resistant cell is a stem cell. In another embodiment, an apoptosis-signaling resistant cell is an immune cell insensitive to activation-induced cell death (AICD). In another embodiment, an apoptosis-signaling resistant cell is a progenitor cell. In another embodiment, an apoptosis-signaling resistant cell is a stem cell, an immune cell insensitive to activation-induced cell death (AICD), a progenitor cell or any combination thereof.

In another embodiment, a stem cell is an umbilical cord blood stem cell. In another embodiment, a stem cell is a mobilized peripheral blood stem cell. In another embodiment, a stem cell is bone marrow stem cell. In another embodiment, a stem cell is a cancer stem cell. In another embodiment, a stem cell is a neural stem cell. In another embodiment, a stem cell is a cord blood stem cell, a mobilized peripheral blood stem cell, a bone marrow stem cell, a cancer stem cell, a neural stem cell or a combination thereof.

In another embodiment, an "immune cell insensitive to activation-induced cell death (AICD)" as used herein refers to cell of the immune system that does not undergo apoptosis upon activation. In another embodiment, an immune cell insensitive to activation-induced cell death (AICD) is a non-activated T cell.

Harvesting of stem-cells for therapeutic purposes requires extraction of a tissue which contains stem-cells, either autologous or from a donor, and then isolation of the stem-cells from other cell populations that may have deleterious effects if co-transplanted along with stem-cells.

In another embodiment, the phrase "apoptosis resistant" is "receptor-mediated apoptosis resistant". In another embodiment, the cell-selection method of the present invention is a single-step negative selection method for cell types that are resistant to receptor-mediated apoptosis. In another embodiment, the present method enables parallel isolation of both stem cells and immune-cells that support the clinical outcome of transplantation, via a single use of the device, as is exemplified below.

According to another embodiment, the cell populations which may be used in the method of the present invention are derived from, but are not limited to, bone marrow, umbilical cord blood (UCB) and progenitor cell mobilized peripheral blood (mPB). However, it is clear to one skilled in the art that the cell population may also be derived from other adult tissues which contain apoptosis-resistant cells. In another embodiment, the cell population derives from embryonic tissue.

In another embodiment, a heterogeneous cell population is derived from an organ or a tissue. In another embodiment, a heterogeneous cell population is derived from an embryo.

In another embodiment, a heterogeneous cell population is derived from a tissue comprising embryonic cells, stem cells, immune cells, or any combination thereof. In another embodiment, a heterogeneous cell population is derived from bone marrow. In another embodiment, a heterogeneous cell population is derived by mechanical dislodgement from the bone marrow stroma by aspiration or by apheresis following mobilization into the peripheral blood (mPB) through activation and disruption of the molecular anchors. In another embodiment, a heterogeneous cell population is derived from peripheral-blood.

In another embodiment, the stem cell is selected from a heterogeneous population of cells. In another embodiment, the phrase "heterogeneous population of cells" as used herein refers to a mixture of cell types comprising a stem cell as defined above and at least one apoptosis-sensitive cell. In another embodiment, the heterogeneous population of cells is derived from any organism. In another embodiment, the heterogeneous population of cells is derived from a mammalian source. In another embodiment, the heterogeneous population of cells is derived from a human source.

In another embodiment, the heterogeneous population of cells comprises a mixture of a lineage positive cell and stem cell. In another embodiment, "a lineage positive cell" as used herein refers to a cell expressing mature cell lineage marker. In another embodiment, a mature cell lineage marker is a Cluster of Differentiation (CD) protein.

In another embodiment, the method of the present invention is used to perform lineage depletion.

In another embodiment, the heterogeneous population of cells is a tissue or a part thereof. In another embodiment, the heterogeneous population of cells is a cell aggregate. In another embodiment, the heterogeneous population of cells is a single cell suspension. In another embodiment, the heterogeneous population of cells is a primary culture. In another embodiment, the heterogeneous population of cells is a cellular sample. In another embodiment, the heterogeneous population of cells comprises ant population which is accessible to the pro-apoptotic agents of the present invention.

According to another embodiment, incubating within the device lasts from 2 hours to 72 hours. In another embodiment, incubating within the device lasts from 2 hours to 4 hours. In another embodiment, incubating within the device lasts from 4 hours to 10 hours. In another embodiment, incubating within the device lasts from 10 hours to 24 hours. In another embodiment, incubating within the device lasts from 12 hours to 36 hours. In another embodiment, incubating within the device lasts from 24 hours to 48 hours. In another embodiment, incubating within the device lasts from 36 hours to 72 hours. In another embodiment, incubating within the device lasts from 48 hours to 72 hours.

Unexpectedly, the inventors found that different incubation times with different combinations of apoptosis-inducing ligands may result in functionally distinctive clinical outcomes. Therefore, incubation time is in accordance of specific use, as is exemplified herein below.

According to another embodiment, the present invention discloses a cell selection kit. In another embodiment, the kit comprises the device of the present invention which further comprises a solution for maintaining the integrity and activity of an apoptosis-inducing ligand. In another embodiment, the kit further comprises an insert with instructions for performing cell selection according to the methods of the invention. In another embodiment, the solution for maintaining the integrity and activity of an apoptosis-inducing ligand is a solution. In another embodiment, the solution is a buffer or media, which enables the activity of the apoptosis-inducing ligands while maintaining their integrity and structure. In another embodiment, the constituents of the solution vary depending on the apoptosis-inducing ligands used. In another embodiment, the solution comprises a protease inhibitor. In another embodiment, the protease inhibitor is selected from, but not limited to: Phenylmethylsulfonyl fluoride, Benzamidine, Pepstatin A, Leupeptin, Aprotinin, Antipain, EDTA, EGTA or any combination thereof. In another embodiment the solution comprises a buffer system selected from, but not limited to TRIS buffer or Glycing-NaOH (Different conditions that affect buffer selection for the stability and activity of proteins is exemplified in Uguw S. O. and Apte S. P., *Pharmaceutical Technology*: 2004; March: 86-113).

In another embodiment, the solution comprises elements which enable and/or promote cell survival, cell growth, cell proliferation, or any combination thereof. In another embodiment, elements which enable and/or promote cell survival, cell growth, cell proliferation, or any combination thereof include: growth media, serum or anti-bacterial agents. According to this embodiment, the solution enables to maintain viability of a cell within the device of the kit.

In another embodiment, the solution comprises factors which enable stem-cell proliferation. In another embodiment, factors which enable stem-cell proliferation are selected from, but are not limited to, growth factors, hormones, enzymes or chemicals.

In another embodiment, the kit further comprises an additional apoptosis-inducing ligand that is added to the device or to the solution, thus rendering the solution as selective towards the apoptosis resistant cells of the invention.

In another embodiment, the kit of the present invention provides flexibility in the identity or concentration of apoptosis-inducing ligands that are added to a population of cells. According to this embodiment, the kit comprises additional containers, each containing a different apoptosis inducing ligand. The kit's user selects the preferred combination of apoptosis-inducing ligands according to the desired use, as is exemplified herein below, introduces the ligands into the device and allows incubation with the ligands.

In another embodiment, the kit of the present invention provides temporal flexibility in addition of the apoptosis-inducing ligands. As is exemplified herein below, different combinations, sequential administration or incubation times of apoptosis-inducing ligands results in a clinically distinct outcome. The kit's user can select the desired order of addition of the apoptosis-inducing ligands and the incubation period with each ligand within the device, thus achieving the clinical outcome of choice.

According to another embodiment, the present invention further discloses a method for improving the clinical outcome of a hematopoietic stem and progenitor cells (HSPC) transplantation. In another embodiment, a cell population comprising HSPC is provided. In another embodiment, the cell population is contacted with an apoptosis-inducing ligand within the device of the present invention and incubated within the device. In another embodiment, surviving cells are retrieved. In another embodiment, retrieved cells are transplanted in a subject.

In another embodiment, allogeneic cord blood is introduced into the device of the kit of the present invention. According to this embodiment, FasL is immobilized on the inner surface of the container. The blood is incubated in the device for less than 24 hours. When the incubation is over, TNF-α is introduced into the device and incubation is continued for 24-48 hours. Following the second incubation the cells are extracted from the device and are transplanted into the patient. In another embodiment, an isolation step is used between the end of incubation and transplantation, in order to isolate the living cells from cell debris and proteins in the solution.

In another embodiment, the cell population of the method in derived of an autologous transplant. In another embodiment, the cell population of the method in derived of an allogeneic transplant.

According to another embodiment, the present invention further discloses a method for eliminating a malignant cell in a composition. In this method, the composition is contacted and incubated with an apoptosis-inducing ligand. In another embodiment, the composition comprises a progenitor-cell transplant.

Figure 15E:
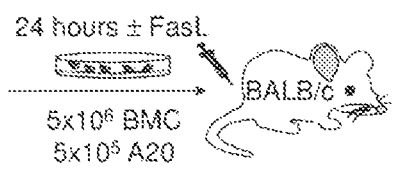
Figure 15F:
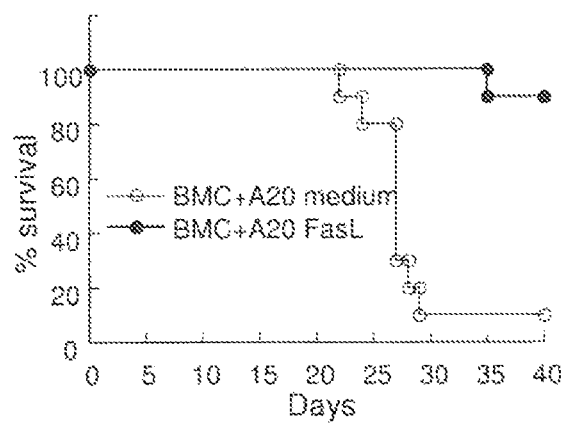

In another embodiment, the apoptosis-inducing ligand is FasL. In another embodiment, the incubation is for about 24 hours. The inventors have shown in-vivo that, unexpectedly, addition of FasL for about 24 hours to a transplant containing a malignant cell eliminates the malignant contaminant and improves survival rate (FIG. 15E-F).

According to another embodiment, this elimination technique has the potential to ensure the absence of malignant cells in grafts from apparently healthy donors that suffer of subclinical malignant disease.

According to another embodiment, a transplant is extracted out of the bone marrow of a cancer-patient and introduced into the device of the present invention. According to this embodiment, the transplant is incubated with immobilized FasL for about 24 hours. Upon completion of the incubation, the selected cells are transplanted back into the cancer patient. In another embodiment, An isolation step precedes transplantation, as so to isolate the selected cells from cell debris and proteins.

According to another embodiment, the present invention further discloses a method for preventing graft vs. host disease (GvHD) while retaining graft vs. tumor (GvT) activity. According to this method, a sample is provided. In one embodiment, the sample comprises a cell population. In another embodiment, the cell population comprises HSPC. In another embodiment, the cell population comprises an immune cell. In another embodiment, the cell population comprises HSPC, an immune cell or a combination thereof. According to one embodiment, the cell population is contacted with an apoptosis-inducing ligand. In another embodiment, surviving cell is retrieved from the device. In another embodiment, retrieved cell is transplanted in a subject.

According to another embodiment, the method of the present invention leads only to selection of T cell subsets that do not induce GvHD. The inventors have found, unexpectedly, that short incubation with FasL, of 2-16 hours, without concurrent T cell sensitization, results in an effective removal of GvHD effectors (FIG. 9). According to this embodiment, survival of T cell subsets which support hematopoietic progenitor engraftment is achieved, as treatment of transplanted cells with FasL did not impair engraftment (FIG. 14).

In another embodiment, the selective elimination of apoptosis-sensitive T cells from the donor inoculum does not impair generation of a potent graft vs. tumor (GvT) reaction.

According to another embodiment, the method of the present invention can be used on an allogeneic mobilized peripheral blood transplant, which is known in the art to suffer from a high degree of GvHD. In this embodiment, the allogeneic mobilized peripheral blood transplant is introduced into the device of the present invention. The transplant is next incubated with immobilized FasL for a short period of 2-16 hours. Following incubation, the remaining cells are retrieved and transplanted into the patient. According to another embodiment, an isolation step may precede the transplantation, as so to isolate the selected cells from cell debris and proteins.

According to another embodiment, the method of the present invention may be used for selective depletion of un-stimulated T cells prior to donor lymphocyte infusion (DLI).

Recombinant Expression According to Some Embodiments

In another embodiment, a protein of the present invention may be synthesized by expressing a polynucleotide molecule encoding the protein in a host cell, for example, a microorganism cell transformed with the nucleic acid molecule.

DNA sequences encoding proteins may be isolated from any cell producing them, using various methods well known in the art (see for example, Sambrook, et al., Molecular Cloning: A Laboratory Manual, Third Edition, Cold Spring Harbor, N.Y., (2001)). For example, a DNA encoding the wild-type protein may be amplified from genomic DNA, plasmid or cosmid of the appropriate microorganism by polymerase chain reaction (PCR) using specific primers, constructed on the basis of the nucleotide sequence of the known sequence. Suitable techniques are well known in the art, described for example in U.S. Pat. Nos. 4,683,195; 4,683,202; 4,800,159 and 4,965,188

The DNA may be extracted from the cell prior to the amplification using various methods known in the art, see for example, Marek P. M et al., "Cloning and expression in *Escherichia coli* of *Clostridium thermocellum* DNA encoding p-glucosidase activity", Enzyme and Microbial Technology Volume 9, Issue 8, August 1987, Pages 474-478.

The isolated polynucleotide encoding the protein may be cloned into a vector, such as the pET28a plasmid.

Upon isolation and cloning of the polynucleotide encoding a protein, mutation(s) may be introduced by modification at one or more base pairs, using methods known in the art, such as for example, site-specific mutagenesis (see for example, Kunkel Proc. Natl. Acad. Sci. USA 1985, 82:488-492; Weiner et al., Gene 1994, 151:119-123; Ishii et al., Methods Enzymol. 1998, 293:53-71); cassette mutagenesis (see for example, Kegler-Ebo et al., Nucleic Acids Res. 1994 May 11; 22 (9):1593-1599); recursive ensemble mutagenesis (see for example, Delagrave et al., Protein Engineering 1993, 6 (3):327-331), and gene site saturation mutagenesis (see for example, U.S. Pat. Application No. 2009/0130718).

Methods are also well known for introducing multiple mutations into a polynucleotide (see for example, Michaelian et al., Nucleic Acids Res. 1992, 20:376; Dwivedi et al., Anal. Biochem. 1994, 221:425-428; Bhat Methods Mol. Biol. 1996, 57:269-277; Meetei et al., Anal. Biochem. 1998, 264:288-291; Kim et al., Biotechniques 2000, 28:196-198; and International patent Application Publication Nos. WO 03/002761A1 and WO 99/25871).

An alternative method to producing a polynucleotide with a desired sequence is the use of a synthetic gene. A polynucleotide encoding a protein of the present invention may be prepared synthetically, for example using the phosphoroamidite method (see, Beaucage et al., Curr Protoc Nucleic Acid Chem. 2001 May; Chapter 3:Unit 3.3; Caruthers et al., Methods Enzymol. 1987, 154:287-313).

The use of synthetic genes allows production of an artificial gene which comprises an optimized sequence of nucleotides to be expressed in desired species (for example, E. coli). Redesigning a gene offers a means to improve gene expression in many cases. Rewriting the open reading frame is possible because of the redundancy of the genetic code. Thus, it is possible to change up to about a third of the nucleotides in an open reading frame and still produce the same protein. For example, for a typical protein sequence of 300 amino acids there are over 10150 codon combinations that will encode an identical protein. Using optimization methods such as replacing rarely used codons with more common codons can result in dramatic effect on levels of expression of protein encoded by the target gene. Further optimizations, such as removing RNA secondary structures, can also be included. Computer programs are available to perform these and other simultaneous optimizations. Because of the large number of nucleotide changes made to the original DNA sequence, the only practical way to create the newly designed genes is to use gene synthesis.

The polynucleotide thus produced may then be subjected to further manipulations, including one or more of purification, annealing, ligation, amplification, digestion by restriction endonucleases and cloning into appropriate vectors. The polynucleotide may be ligated either initially into a cloning vector, or directly into an expression vector that is appropriate for its expression in a particular host cell type.

As is readily apparent to those skilled in the art, the codon used in the polynucleotide for encoding a particular amino acid which is to substitute an amino acid originally present in the sequence encoding the wild-type enzyme, should be selected in accordance with the known and favored codon usage of the host cell which was selected for expressing the polynucleotide.

A skilled person is aware of the relationship between nucleic acid sequence and protein sequence, in particular, the genetic code and the degeneracy of this code, and will be able to construct nucleic acids encoding the proteins of the present invention without difficulty. For example, a skilled person will be aware that for each amino acid substitution in a protein sequence, there may be one or more codons which encode the substitute amino acid. Accordingly, it will be evident that, depending on the degeneracy of the genetic code with respect to that particular amino acid residue, one or more nucleic acid sequences may be generated corresponding to a certain variant protein sequence.

The polynucleotides of the present invention may include non-coding sequences, including for example, non-coding 5' and 3' sequences, such as transcribed, non-translated sequences, termination signals, ribosome binding sites, sequences that stabilize mRNA, introns and polyadenylation signals. Further included are polynucleotides that comprise coding sequences for additional amino acids heterologous to the variant protein, in particular a marker sequence, such as a poly-His tag, that facilitates purification of the protein in the form of a fusion protein.

Proteins of the invention may be produced as tagged proteins, for example to aid in extraction and purification. A non-limiting example of a tag construct is His-Tag (six consecutive histidine residues), which can be isolated and purified by conventional methods. It may also be convenient to include a proteolytic cleavage site between the tag portion and the protein sequence of interest to allow removal of tags, such as a thrombin cleavage site.

The polynucleotide encoding the protein of the invention may be incorporated into a wide variety of expression vectors, which may be transformed into in a wide variety of host cells. The host cell may be prokaryotic or eukaryotic.

Introduction of a polynucleotide into the host cell can be effected by well-known methods, such as chemical transformation (e.g. calcium chloride treatment), electroporation, conjugation, transduction, calcium phosphate transfection, DEAE-dextran mediated transfection, transvection, microinjection, cationic lipid-mediated transfection, scrape loading, ballistic introduction and infection.

In some embodiments, the cell is a prokaryotic cell. Representative, non-limiting examples of appropriate prokaryotic hosts include bacterial cells, such as cells of *Escherictahia coli* and *Bacillus subtilis*. In other embodiments, the cell is a eukaryotic cell. In some exemplary embodiments, the cell is a fungal cell, such as yeast. Representative, non-limiting examples of appropriate yeast cells include *Saccharomyces cerevisiae* and *Pichia pastoris*. In additional exemplary embodiments, the cell is a plant cell.

The proteins may be expressed in any vector suitable for expression. The appropriate vector is determined according the selected host cell. Vectors for expressing proteins in *E. coli*, for example, include, but are not limited to, pET, pK233, pT7 and lambda pSKF. Other expression vector systems are based on beta-galactosidase (pEX); maltose binding protein (pMAL); and glutathione S-transferase (pGST).

Selection of a host cell transformed with the desired vector may be accomplished using standard selection protocols involving growth in a selection medium which is toxic to non-transformed cells. For example, *E. coli* may be grown in a medium containing an antibiotic selection agent; cells transformed with the expression vector which further provides an antibiotic resistance gene, will grow in the selection medium.

Upon transformation of a suitable host cell, and propagation under conditions appropriate for protein expression, the desired protein may be identified in cell extracts of the transformed cells. Transformed hosts expressing the protein of interest may be identified by analyzing the proteins expressed by the host using SDS-PAGE and comparing the gel to an SDS-PAGE gel obtained from the host which was transformed with the same vector but not containing a nucleic acid sequence encoding the protein of interest.

The protein of interest can also be identified by other known methods such as immunoblot analysis using suitable antibodies, dot blotting of total cell extracts, limited proteolysis, mass spectrometry analysis, and combinations thereof.

The protein of interest may be isolated and purified by conventional methods, including ammonium sulfate or ethanol precipitation, acid extraction, salt fractionation, ion exchange chromatography, hydrophobic interaction chromatography, gel permeation chromatography, affinity chromatography, and combinations thereof.

The isolated protein of interest may be analyzed for its various properties, for example specific activity and thermal stability, using methods known in the art, some of them are described hereinbelow.

Conditions for carrying out the aforementioned procedures as well as other useful methods are readily determined by those of ordinary skill in the art (see for example, Current Protocols in Protein Science, 1995 John Wiley & Sons).

In particular embodiments, the proteins of the invention can be produced and/or used without their start codon (methionine or valine) and/or without their leader (signal) peptide to favor production and purification of recombinant proteins. It is known that cloning genes without sequences encoding leader peptides will restrict the proteins to the cytoplasm of the host cell and will facilitate their recovery (see for example, Glick, B. R. and Pasternak, J. J. (1998) In "Molecular biotechnology: Principles and applications of recombinant DNA", 2nd edition, ASM Press, Washington D.C., p. 109-143).

Synthetic Production According to Some Embodiments

The proteins of the present invention may be synthesized by any techniques that are known to those skilled in the art of protein synthesis. For solid phase protein synthesis, a summary of the many techniques may be found in: Stewart, J. M. and Young, J. D. (1963), "Solid Phase Peptide Synthesis," W. H. Freeman Co. (San Francisco); and Meienhofer, J (1973). "Hormonal Proteins and Peptides," vol. 2, p. 46, Academic Press (New York). For a review of classical solution synthesis, see Schroder, G. and Lupke, K. (1965). The Peptides, vol. 1, Academic Press (New York).

In general, peptide synthesis methods comprise the sequential addition of one or more amino acids or suitably protected amino acids to a growing peptide chain. Normally, either the amino or the carboxyl group of the first amino acid is protected by a suitable protecting group. The protected or derivate amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth; traditionally this process is accompanied by wash steps as well. After all of the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide, and so forth.

Further description of peptide synthesis is disclosed in U.S. Pat. No. 6,472,505.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Sequences

| SEQ ID No. | Identification | Sequence |
|---|---|---|
| 1 | Human FasL | MQQPFNYPYPQIYWVDSSASSPWAPPGTVLPCPTSVPR RPGQRRPPPPPPPPLPPPPPPPLPPLPLPP LKKRGNHSTGLCLLVMFFMVLVALVGLGLGMFQLFHLQ KELAELRESTSQMHTASSLEKQIGHPSPPPEK KELRKVAHLTGKSNSRSMPLEWEDTYGIVLLSGVKYKK GGLVINETGLYFVYSKVYFRGQSCNNLPLSHK VYMRNSKYPQDLVMMEGKMMSYCTTGQMWARSSYLGAV FNLTSADHLYVNVSELSLVNFEESQTFFGLYK |
| 2 | Human TNF-α | MSTESMIRDVELAEEALPKKTGGPQGSRRCLFLSLSF LIVAGATTLFCLLHFGVIGPQREEFPRDLSLI SPLAQAVRSSSRTPSDKPVAHVVANPQAEGQLQWLNRR ANALLANGVELRDNQLVVPSEGLYLIYSQVLF KGQGCPSTHVLLTHTISRIAVSYQTKVNLLSAIKSPCQ RETPEGAEAKPWYEPIYLGGVFQLEKGDRLSA EINRPDYLDFAESGQVYFGIIAL |
| 3 | Human Trail | MAMMEVQGGPSLGQTCVLIVIFTVLLQSLCVAVTYVYF TNELKQMQDKYSKSGIACFLKEDDSYWDPNDE ESMNSPCWQVKWQLRQLVRKMILRTSEETISTVQEKQQ NISPLVRERGPQRVAAHITGTRGRSNTLSSPN SKNEKALGRKINSWESSRSGHSFLSNLHLRNGELVIHE KGFYYIYSQTYFRFQEEIKENTKNDKQMVQYI YKYTSYPDPILLMKSARNSCWSKDAEYGLYSIYQGGIF ELKENDRIFVSVTNEHLIDMDHEASFFGAFLV |
| 4 | Human Tweak | MAARRSQRRRGRRGEPGTALLVPLALGLGLALACLGLL LAVVSLGSRASLSAQEPAQEELVAEEDQDPSE LNPQTEESQDPAPFLNRLVRPRRSAPKGRKTRARRAIA AHYEVHPRPGQDGAQAGVDGTVSGWEEARINS SSPLRYNRQIGEFIVTRAGLYYLYCQVHFDEGKAVYLK LDLLVDGVLALRCLEEFSATAASSLGPQLRLC QVSGLLALRPGSSLRIRTLPWAHLKAAPFLTYFGLFQV H |

EXAMPLE 1

Ex vivo Exposure of Umbilical Cord Blood Cells to Death Ligands

Apoptotic Activity of Death Receptor Activation In vitro

Figure 1B:
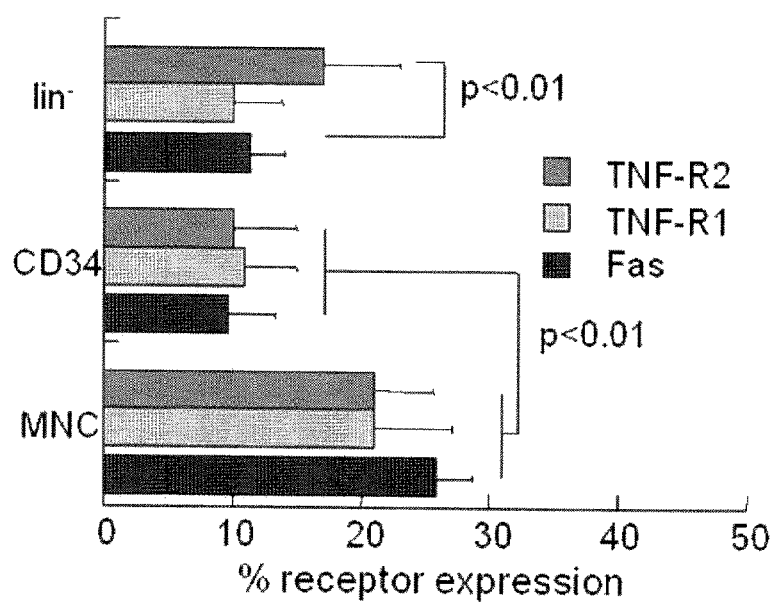
Figure 1C:
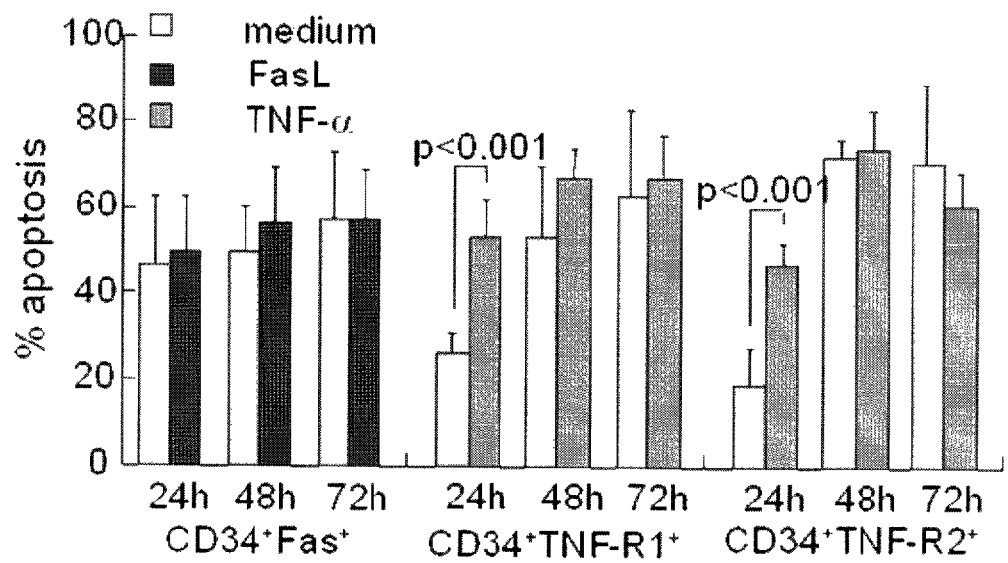
Figure 1D:
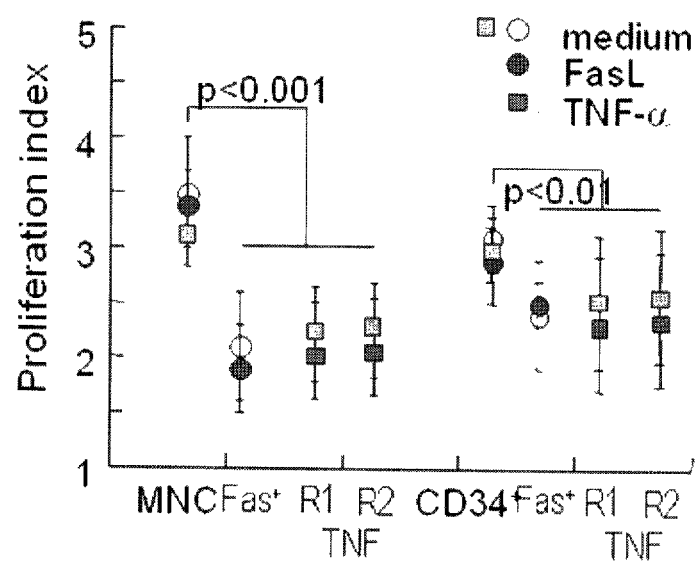

The primary activity of the TNF superfamily is transduction of apoptotic signals. Fresh umbilical cord blood (UCB) obtained from term deliveries upon informed consent were exposed to FasL and TNF-α for various periods of time in liquid culture without supplementation of growth factors. Gated CD34$^+$ progenitors within the bulk UCB cultures displayed reduced rates of apoptosis, with increasing susceptibility as a function of time (FIG. 1A), however apoptotic cell death is not enhanced by exposure to death ligands of the TNF family. It has been previously suggested that insensitivity to apoptotic signaling is caused by low-level expression of the receptors in hematopoietic progenitors. The analysis revealed lower expression of the Fas and TNF receptors in gated CD34$^+$ and isolated lin$^-$ progenitors than in the bulk UCB population (FIG. 1B). More focused evaluation of subsets of cells expressing the receptors showed excessive susceptibility to apoptosis of CD34$^+$ progenitors, however apoptosis was not induced by the cognate receptors with one exception (FIG. 1C). Short-term exposure to TNF-α (<24 hours) was the only case of detectable receptor-mediated apoptosis of CD34$^+$ cells expressing both TNF-R1 and TNF-R2. These data suggest that expression of the death receptors is a characteristic of cells that are particularly susceptible to spontaneous apoptosis in liquid culture. The variations in apoptosis might originate from differential rates of proliferation, however increased susceptibility to apoptosis of receptor-positive CD34$^+$ progenitors were associated with reduced proliferation rates that were also unaffected by the presence of the cognate ligands (FIG. 1D).

Figure 1E:
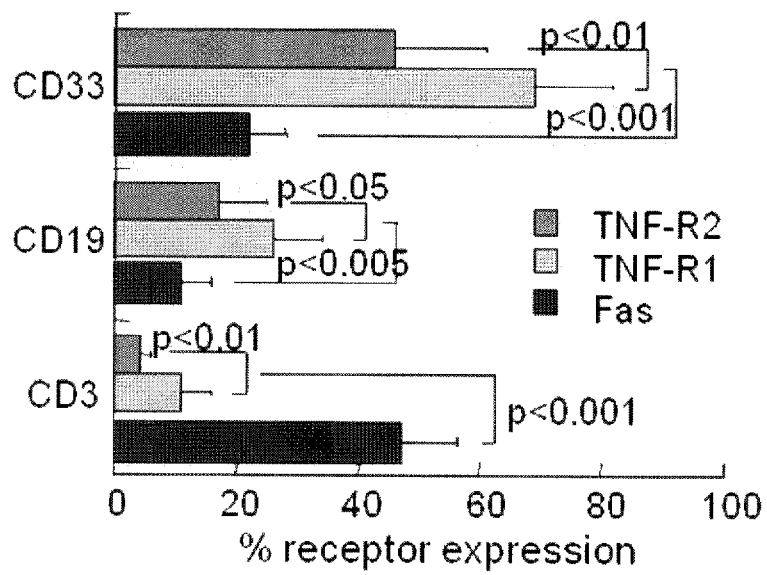
Figure 1F:
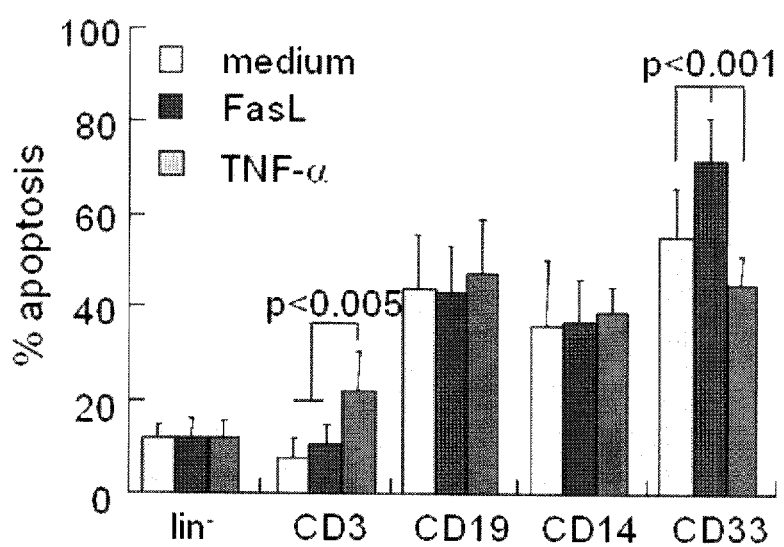

To define which subsets of UCB cells are susceptible to apoptosis, the myeloid and lymphoid lineages were further assessed. Whereas CD3$^+$ T cells express high levels of Fas, the TNF receptors are dominant in CD33$^+$ myeloid cells (FIG. 1E). TNF-R1 is in general expressed at higher levels than TNF-R2 in all the lineage-positive subsets. Exposure to the apoptotic challenge with death ligands for 48 hours revealed excessive rates of spontaneous apoptosis of all lineage-positive subsets as compared to lin$^-$ progenitors, which were largely unaffected by the presence of ligands (FIG. 1F). Two notable exceptions were observed: a) Fas-mediated apoptosis in $CD14^-CD33^+$ myeloid cells, corresponding to UCB neutrophils, which express high levels of the TNF receptors; and b) TNF-induced apoptosis in $CD3^+$ T cells. Resistance of UCB-derived T cells to apoptosis in liquid culture is explained by the naïve nature of this antigen-inexperienced subset, which requires stimulation in order to sensitize to AICD-type negative regulation. Therefore, apoptosis of unstimulated UCB cells in culture is governed by death of $CD19^+$ B lymphocytes and myeloid cells ($CD14^+$, $CD33^+$), with selective apoptotic functions of the TNF family receptors in the different subsets.

Figure 2A:
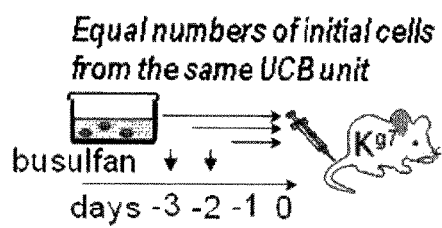
FIG. 2A is a scheme and FIGS. 2B-2G are graphs showing that UCB progenitors are resistant to receptor-mediated apoptosis. (A) NOD.CID mice were conditioned with two doses of 25 μg/g busulfan and were grafted after 2 days with equal numbers of UCB cells incubated under different conditions. Human chimerism was measured in the bone marrow after 12 weeks using selective human and murine anti-CD45 antibodies. (B) Engraftment of fresh UCB cells and following 24 hours of incubation in medium, with 50 ng/ml FasL and 20 ng/ml TNF-α from the same UCB unit. Data are representative of 7 different UCB samples. (C) Engraftment following 48 hours of incubation in medium, with FasL and TNFα from the same UCB unit (representative of 6 UCB samples). (D) Incubation for 72 hours in medium, with FasL and TNFα from the same UCB unit diminishes engraftment (representative of 5 UCB samples). (E) Proliferation rates of mononuclear cells (MNC), gated CD34$^+$ and isolated lineage-negative (lin$^-$) progenitors after 48 hours of incubation in medium, with FasL and TNF-α (n=4-7). (F) Fractions of mitotically-quiescent UCB subsets positioned in the G0/G1 cell cycle phase as determined from nuclear incorporation of propidium iodide (n=5-8). (G) Long-term culture initiating cell (LTC-IC) frequency determined after plating of $10^3$ UCB cells over mesenchymal stromal cell layers for 5 weeks and subsequently transferred to semisolid methylcellulose cultures. FasL (50 ng/ml) and TNF-α (20 ng/ml) were present throughout the entire culture period and were refreshed at weekly intervals by exchange of half of the medium (n=8-13). Data represent comparative culture conditions of one UCB unit.
Figure 2B:
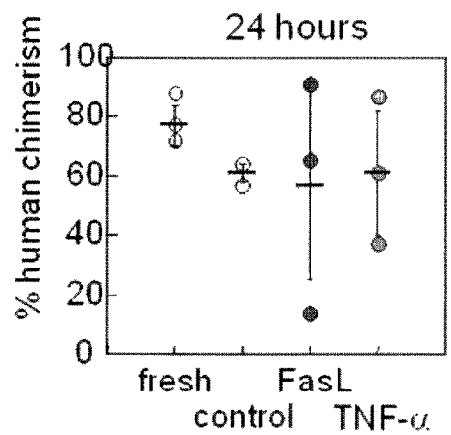
Figure 2C:
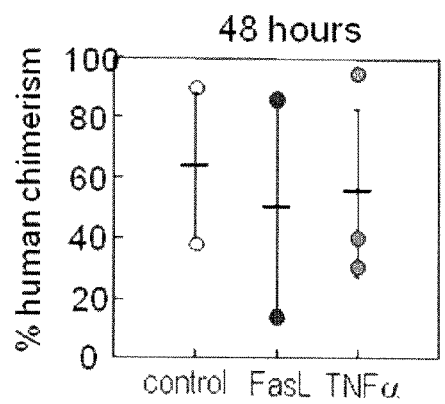
Figure 2D:
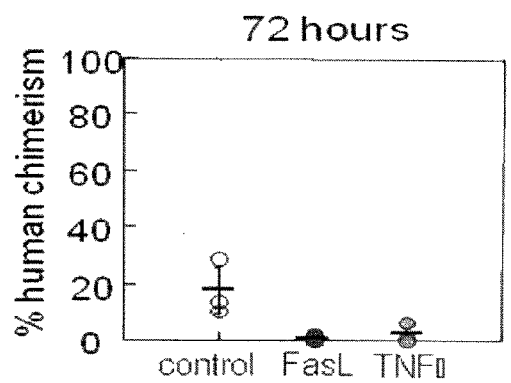
Figure 2E:
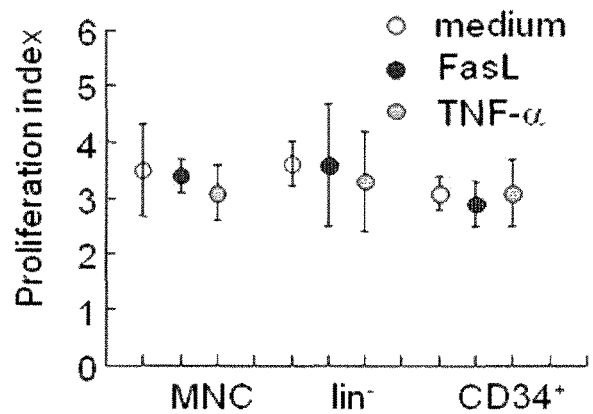

SCID Repopulating Cells and Long-Term Culture Initiating Cells are Resistant to Receptor-Mediated Apoptosis Several surrogate assays were employed to evaluate the function of progressively committed progenitors, including SCID repopulating cells (SRC), long-term initiating cells (LTC-IC) and short-term clonogenic assays. SRC activity is partially compatible with the human reconstituting cell and serves as a surrogate functional assay for the most primitive progenitors within the sample. Equal initial numbers of cells incubated with and without FasL and TNF-α prior to transplantation were used, because the wide variability in levels of xenochimerism precludes precise evaluation of enhanced engraftment (FIG. 2A). SRC function was preserved after exposure to FasL and TNF-α for 24-48 hours prior to transplantation (FIG. 2B-D), indicating that the most primitive hematopoietic precursors were insensitive to spontaneous and receptor-mediated apoptosis in liquid culture. Extended ex vivo incubation is associated with loss of engraftment capacity of human hematopoietic progenitors, irrespective of the presence of FasL and TNF-α (FIG. 2E). Prolonged ex vivo incubation of UCB cells in liquid medium supplemented with chemokines and growth factors is associated with dramatic changes in phenotype and is known to decrease cell homing and engraftment in immunocompromized mice. However, unlike prior studies that attributed deficient SRC engraftment to receptor-mediated apoptosis by death ligands, the detrimental influences of extended culture are largely independent of activation of membranal death receptors.

Figure 2F:
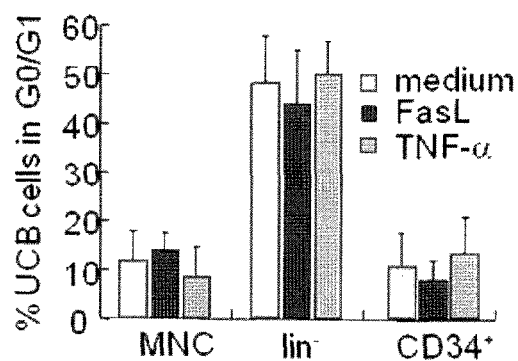

Deficient human cell engraftment after extended periods of ex vivo culture is associated with proliferation and egress from the G0/G1 cell cycle phase. Both the proliferation rates (FIG. 2E) and the cell cycle phase (FIG. 2F) of UCB cells, $CD34^+$ and $lin^-$ progenitors were unaffected by the presence of FasL and TNF-α after 48 hours of incubation. Preservation the high fractions of mitotically-quiescent progenitors in the presence of the death ligands explains equal levels of SRC engraftment, which is restricted to cells positioned in G0/G1.

Figure 2G:
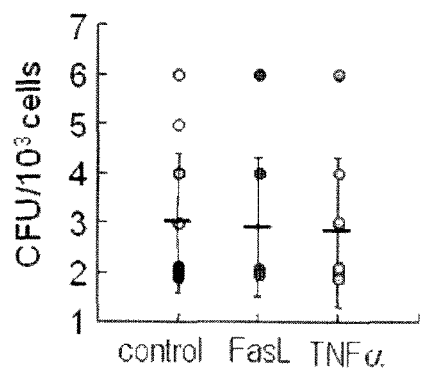

Surrogate ex vivo assays for hematopoietic progenitor activity include long-term cultures over mesenchymal stromal cells (LTC-IC), which represent a more primitive subset than colonies formed by committed progenitors in semisolid methylcellulose cultures. Exposure to FasL and TNF-α at concentrations that are toxic to somatic cells during the entire 5 weeks period of the long-term cultures did not impact LTC-IC activity (FIG. 2G), consistent with overall resistance of the $CD34^+$ and $lin^-$ progenitors to Fas and TNF receptors-mediated apoptotic signaling. Thus, despite remarkable modulation in composition of viable subsets during exposure to the death ligands caused by differential inherent susceptibilities of various UCB subsets to apoptosis, SRC and LTC-IC activities of the most primitive progenitors are preserved, reflecting resistance to receptor-mediated apoptosis.

Enrichment of Myeloid Progenitors by Elimination of Dead Cells

Figure 3A:
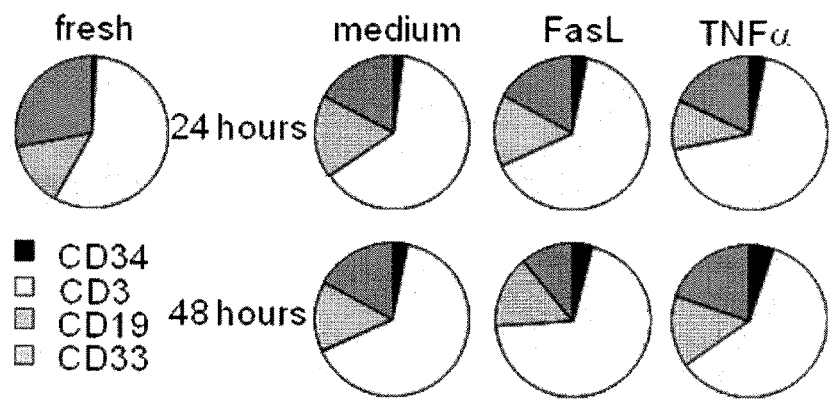
FIG. 3B is a scheme and FIGS. 3A and 3C are graphs showing that exposure of UCB cells to death ligands increases the frequency of progenitors in vitro and myeloid differentiation in vivo. (A) Expression of lineage markers in fresh UCB cells: progenitors (CD34), T cells (CD3), B lymphocytes (CD19) and myeloid cells (CD33). The composition of viable cells changes after incubation for 24 and 48 hours with exposure to 50 ng/ml FasL and 20 ng/ml TNF-α, increasing the fraction of progenitors (n=17-31). (B) Following incubation for variable periods of time the dead cells were eliminated by centrifugation over ficoll gradient and equal numbers of viable cells were plated in semisolid methylcellulose cultures stimulated with stem cell factor (SCF), interleukin-3 (IL-3) and granulocyte-macrophage colony stimulating factor (GM-CSF). The frequency of colony forming cells (CFU, expressed per $10^3$ viable cells) was determined after 14 days. (C) Relative CFU frequencies in fresh UCB samples (control) and after incubation in medium, with FasL and TNF-α (n=12-27).
Figure 3B:
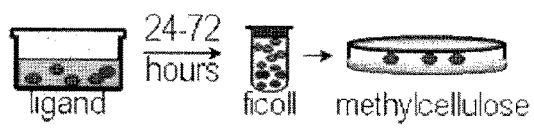
Figure 3C:
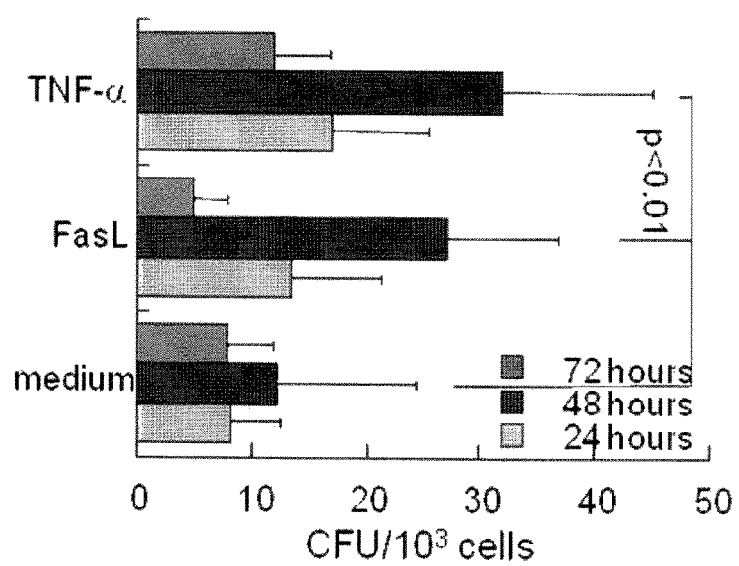

Inherent susceptibility to spontaneous and receptor-induced apoptosis of various subsets of UCB cells results in marked variations in the composition of viable cells after ex vivo incubation. For example, following 48 hours of incubation with toxic doses of FasL there is marked enrichment in viable lineage-negative cells, whereas incubation with TNF-α results in relative enrichment in viable myeloid cells (FIG. 3A). It was reasoned that the enrichment in progenitors following exposure to death ligands would augment clonogenic activity in semisolid cultures. Variations in colony forming unit (CFU) frequency can be evaluated following removal of dead cells by sedimentation over ficoll and plating of equal numbers of viable UCB cells in semisolid methylcellulose cultures (FIG. 3B) stimulated with stem cell factor (SCF), interleukin-3 (IL-3) and granulocyte-macrophage colony stimulating factor (GM-CSF). Consistent with predominant apoptosis of mature UCB cells, CFU-GM frequency increased from 1:143 in control cultures to 1:37 and 1:31 after 48 hours of exposure to FasL and TNF-α, respectively (FIG. 3C). While maximal enrichment was observed after 48 hours of incubation, extended ex vivo culture beyond this period had detrimental consequences on the function of committed myeloid progenitors. This assay uncovers selective receptor-mediated elimination of non-progenitor cells in UCB samples, which despite similar overall rates of apoptosis results in 4-5 fold increase in CFU-GM frequency.

Cross-Talk Between TNF Family Receptors does not Sensitize to Apoptosis

Figure 4A:
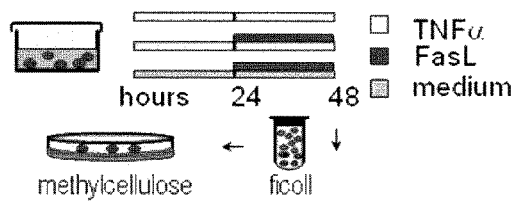
FIG. 4A is a scheme and FIGS. 4B-4D are graphs showing the combined effects of death ligands on UCB cells. (A) Expression of Fas was stimulated by incubation with 20 ng/ml TNF-α for 24 hours and subsequently cells were incubated for additional 24 hours with and without 50 ng/ml FasL. (B) Fas expression in mononuclear cells (MNC) and gated CD34$^+$ progenitors under the various incubation conditions (n=6-9). (C) Apoptosis of Fas-positive MNC, gated CD34$^+$ and isolated lineage-negative (lin$^-$) progenitors during 48 hours of incubation with TNF-α, with and without supplementation of FasL (n=5-12). (D) CFU frequencies in bulk cell suspensions after various incubations increases after elimination of dead cells by centrifugation over ficoll (n-7-15).
Figure 4B:
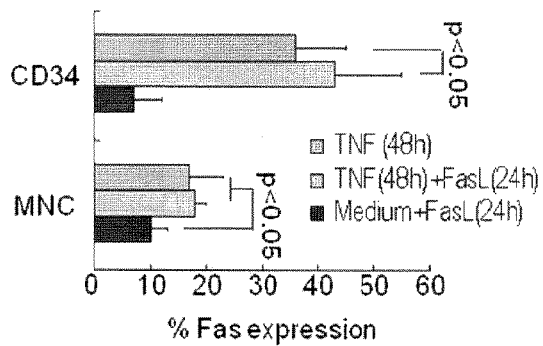
Figure 4C:
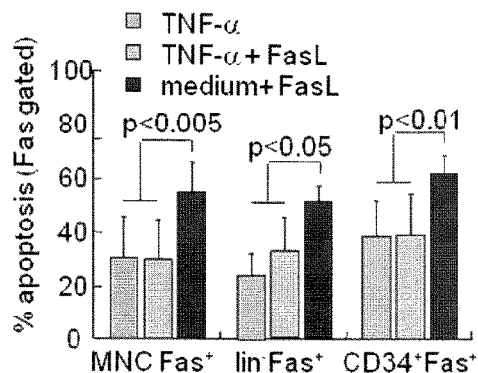
Figure 4D:
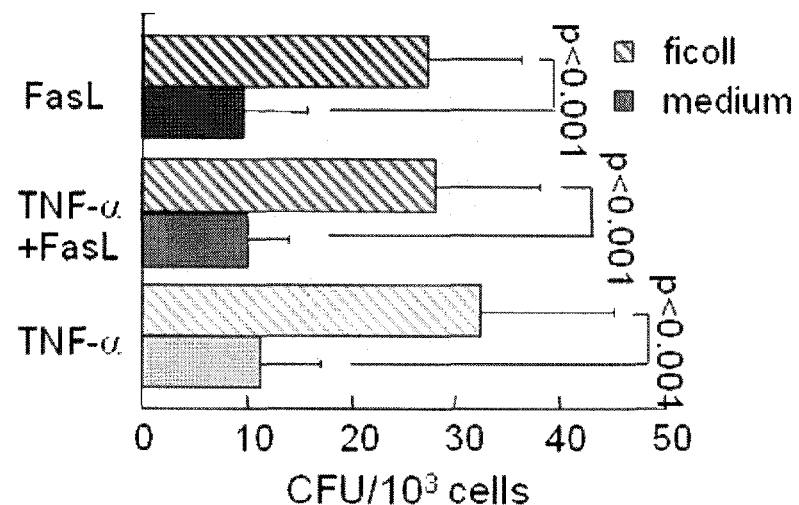

The TNF family receptor/ligand interactions are characterized by partial homology but distinct specificity of receptor activation. Most ligands bind several cognate receptors, however there is no known cross-activation of receptors by several ligands. Cross talk in this family is therefore mediated by induced upregulation of receptors in response to activation of another TNF family receptor. The best known example of cross talk is induced expression of Fas upon TNF receptor activation in $CD34^+$ progenitors. To determine whether TNF-induced Fas expression sensitized UCB cells to apoptosis, cells were first exposed to TNF-α and then exposed to FasL (FIG. 4A), resulting in marked upregulation of the Fas receptor (FIG. 4B). Whereas $Fas^+$ cells were induced into apoptosis by exposure to FasL during the second day of culture, UCB cells, gated $CD34^+$ and isolated $lin^-$ progenitors were relatively protected by the presence of TNF-α (FIG. 4C), indicating that upregulation of Fas expression was dissociated from the sensitivity to apoptosis. Functional assays of progenitor enrichment by ligand-mediated elimination of apoptosis-sensitive cells showed that joint exposure to FasL and TNF-α increase CFU-GM frequency (FIG. 4D) and consistently, joint exposure of UCB cells to both ligands did not impair SRC activity in vivo (not shown). These data document resistance of hematopoietic progenitors to apoptotic signal transduction by two independent pathways, their joint activation, and crosstalk between TNF family receptors.

Depletion of Differentiating Cells During Ex vivo Expansion of UCB Cells

Figure 5A:
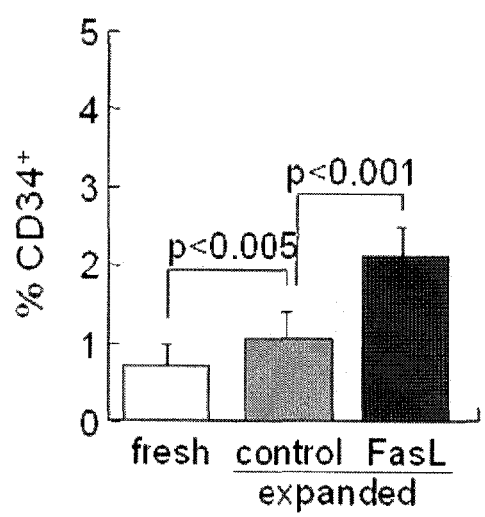
FIG. 5C is a scheme and FIGS. 5A, 5B and 5D are graphs showing that death ligands increase progenitor frequency during ex vivo expansion of UCB cells. (A) CD34$^+$ progenitors were immunomagnetically isolated and expanded under a clinically approved protocol for 3 weeks in liquid culture. The fraction of CD34$^+$ progenitors increased during expansion as compared to the fresh UCB sample and further increased upon supplementation of 50 ng/ml FasL during the third and final week of culture (n=4). (B) Absolute numbers of CD34$^+$ cells in cultures after 3 weeks of expansion (n=4) normalized for $10^3$ total cells. (C) Equal numbers of fresh and expanded UCB cells (from same sample) were grafted into NOD.SCID mice (H2K$^{g7}$) conditioned with two doses of 25 μg/g busulfan. (D) Human hematopoietic chimerism was determined in the bone marrow and spleen after 12 weeks. Data are representative of 6 independent UCB units comparing fresh cells, expanded progenitors with and without FasL during the final third week of culture.
Figure 5B:
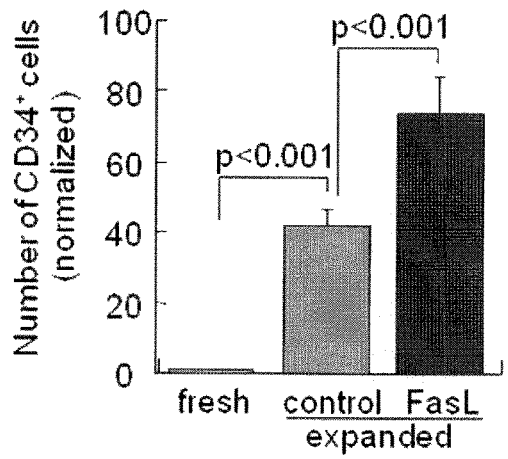
Figure 5C:
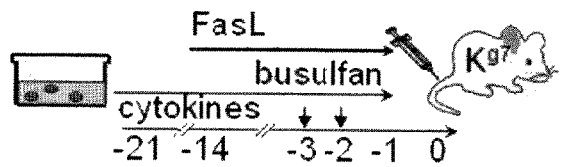
Figure 5D:
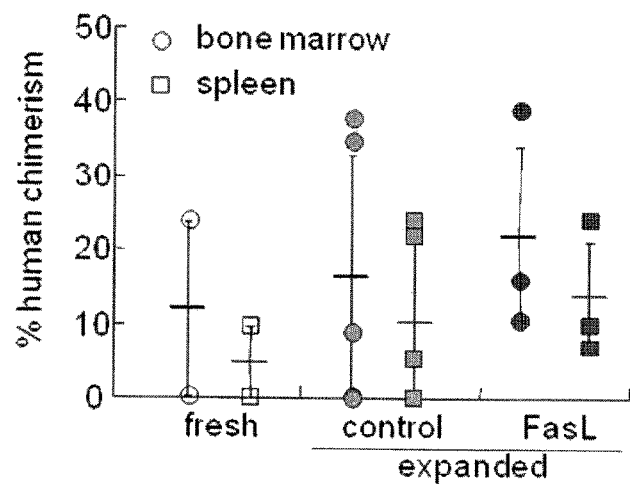

Umbilical cord blood is a good source of hematopoietic progenitors for reconstitution of the immuno-hematopoietic system after aggressive radiochemotherapy, however has two major disadvantages: small number of cells and slow engraftment. To overcome these limitations, a number of approaches to ex vivo expansion of UCB cells prior to transplantation have been developed. The cells are numerically expanded and progenitors become activated, which improve the quality of hematopoietic reconstitution. It was reasoned that exposure of the cell cultures to TNF-family ligands will award a relative advantage to more primitive progenitors by limitation of the clonal expansion of differentiated cells, which do not impact significantly the efficiency of engraftment. Using a standard expansion protocol that increases the fraction (FIG. 5A) and absolute numbers of $CD34^+$ progenitors (FIG. 5B), supplementation FasL during the third and final week of ex vivo culture resulted in further significant expansion of the $CD34^+$ subset. To determine the frequency and function of SRC, the most primitive assay for human hematopoietic progenitors, equal numbers of UCB cells from the same UCB unit were grafted into Busulfan-conditioned immunocompromized NOD.SCID mice (FIG. 5C). Exposure to FasL during the third week of culture resulted in equal and/or higher levels of human hematopoietic xenochimerism (FIG. 5D), emphasizing that the function of progenitors was improved. The wide variability of engraftment in individual mice precludes more accurate determination of superior functionality of the increased numbers of expanded $CD34^+$ progenitors. Thus, selective depletion of apoptosis-sensitive cells is an effective way to increase the fractions and numbers of ex vivo expanded UCB progenitors for transplantation.

EXAMPLE 2

Ex Vivo Exposure of Mobilized Peripheral Blood Cells to Death Ligands

Apoptotic Activity of Death Receptor Activation In vitro

Figure 6A:
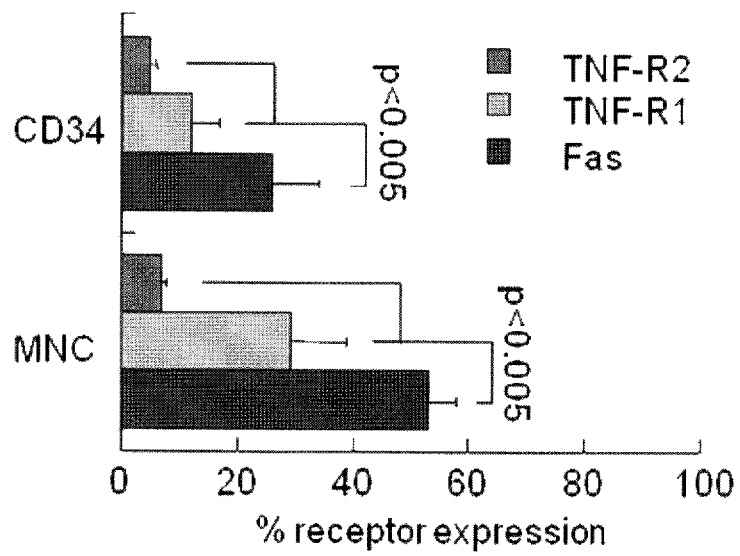
FIGS. 6A-6F are graphs showing the expression of death receptors and sensitivity to apoptosis of mPB cells during brief culture. mPB samples cryopreserved for 2-7 years were thawed, excess DMSO was removed and cells were incubated for 4 and 16 hours with and without 50 ng/ml FasL and 29 ng/ml TNF-α. (A) Expression of Fas and TNF receptors in mononuclear (MNC) mPB cells and gated CD34$^+$ progenitors (n=7-11). (B) Comparative analysis of Fas and TNF receptor expression in lineage-positive T cells (CD3), B lymphocytes (CD19) and myeloid cells (CD33) (n=7-11). (C) Fas expression decreases substantially during 16 hours of culture in all subsets (n=5-9). (D) Upregulation of TNF-R2 during culture most prominent in B lymphocytes (CD19) and myeloid cells (CD33) (n=7-11). (E) Thawed mPB samples were incubated for 4 and 16 hours with and without FasL and TNF-α (n=5-11). Apoptosis was determined from Annexin-V incorporation. (F) Comparative rates of apoptosis of gated CD34$^+$ progenitors and CD3$^+$ T cells following incubation of thawed mPB for 4 and 16 hours with and without the death ligands.
Figure 6B:
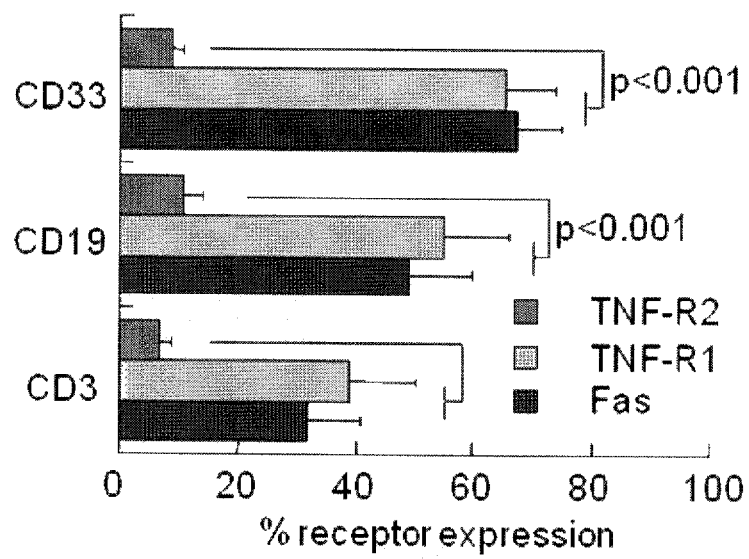
Figure 6C:
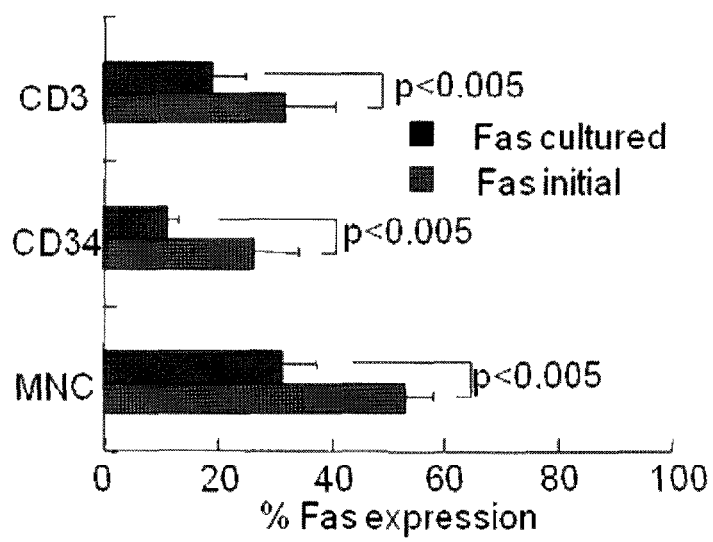
Figure 6D:
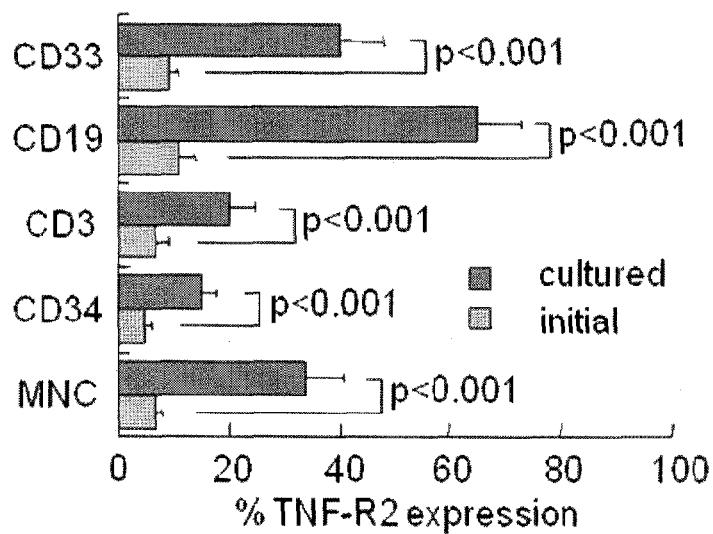

A prevalent source of hematopoietic progenitors for transplantation is peripheral blood following mobilization with granulocyte colony stimulating factor (G-CSF) or antagonists of c-kit and CXCR4. The mobilized mononuclear cells are subsequently collected from peripheral blood by apheresis, containing a substantial number of $CD34^+$ progenitors. Cells harvested from the peripheral blood are generally activated, therefore the periods of exposure to death ligands for selective depletion are significantly shorter. An additional difference from data presented for UCB cells is the use of cryopreserved mPB samples, the thawing of which is associated with apoptotic death of 15-25% of the cells. Fas is expressed in ~25% of $CD34^+$ progenitors (FIG. 6A) and considerable fractions of B lymphocytes and myeloid cells (50-65%, FIG. 6B). The TNF receptors are expressed primarily in lineage-positive mPB cells with predominant expression of TNF-R1. Following brief culture Fas expression decreases (FIG. 6C), whereas all subsets display marked upregulation of TNF-R2 (FIG. 6D). These data disclose dynamic variations in death receptor expression in thawed mPB cells, which is affected on the one hand by death of $Fas^+$ cells and on the other hand by upregulation of TNF-R2.

Figure 6E:
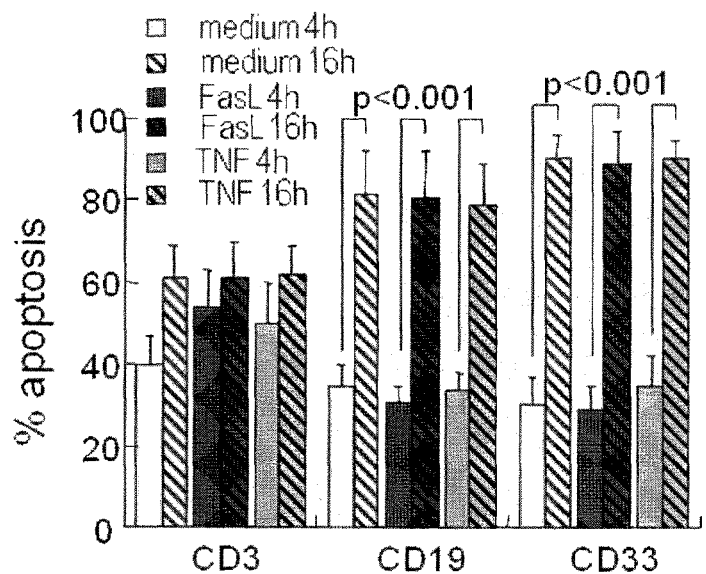
Figure 6F:
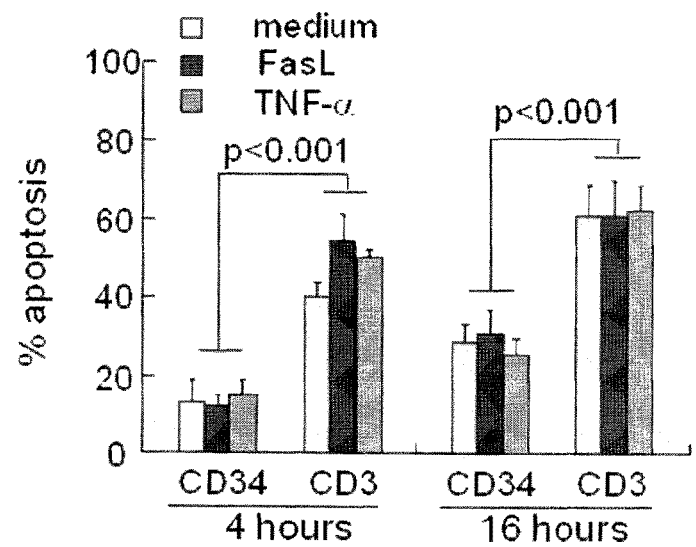

Whereas 25-45% of lineage-positive cells are apoptotic within 4 hours of ex vivo incubation, 60-90% of these cells are induced into apoptosis within 16 hours of incubation (FIG. 6E). The presence of FasL and TNF-α does not attenuate significantly the high rates of apoptosis of lineage-positive cells observed in medium. The most prominent variation from UCB cells is the activated $CD3^+$ T cell subset in mobilized peripheral blood (mPB), which is induced into apoptosis by the ligands within a short period of time. These relative sensitivities to receptor-mediated apoptosis result in significant changes in composition of viable cells, with remarkable reduction in T cells following 4 hours of incubation and of B lymphocytes and myeloid cells following 16 hours of incubation. At both time points $CD3^+$ T cells are selectively depleted, enriching the viable fraction with $CD34^+$ progenitors (FIG. 6F). Therefore, brief incubation of mobilized peripheral blood with death ligands depletes subsets of mature cells and enriches progenitors in cryopreserved mPB samples.

Figure 7A:
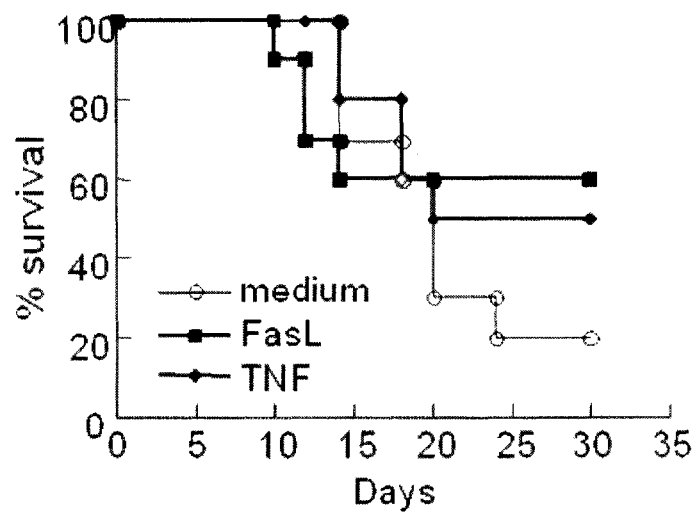
FIGS. 7A-7D are graphs showing that death ligands prevent GvHD in transplants of cryopreserved mobilized peripheral blood (mPB). (A) Survival of NOD.SCID mice conditioned with two doses of 25 μg/g and grafted after 2 days with 1.5×10$^7$ mPB cells incubated in medium with 50 ng/ml FasL and 20 ng/ml TNFα for 4 hours (n=10 in each group). (B) Human xenochimerism was measured in the bone marrow at 12 weeks post-transplantation of cells from the same mPB sample with (n=10) and without (n=7) preincubation with FasL. (C) Body weight at three weeks post-transplantion in recipients of thawed cells (n=18) and after incubation for 4 hours in medium (n=12), with and without FasL (n=9) and TNFα (n=10). At the experimental point of 12 weeks mice grafted with cells incubated in medium and with FasL were assessed for: (D) clinical score according to normal (0) and abnormal (1) parameters: 1. skin disease and hair loss, 2. weakness, 3. footpad hyperkeratosis and 4. diarrhea, and (E) liver histology scored according to: 0-no infiltration, 1-scarce infiltrates, 2-patchy infiltration, 3-diffuse infiltration, 4-deterioration of tissue infrastructure.
Figure 7B:
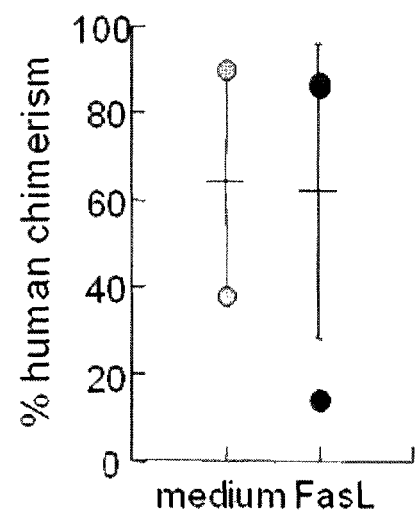
Figure 7C:
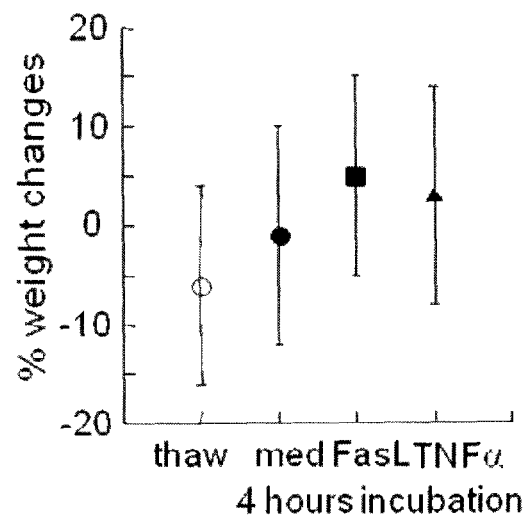
Figure 7D:
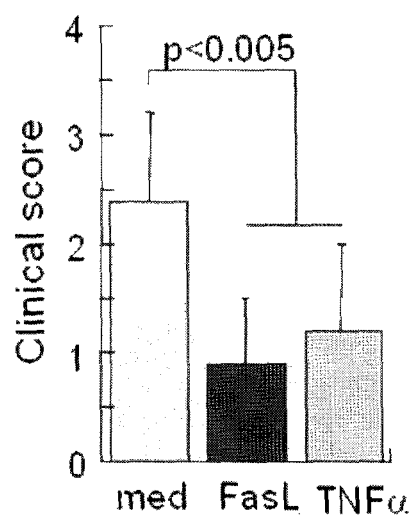
Figure 7E:
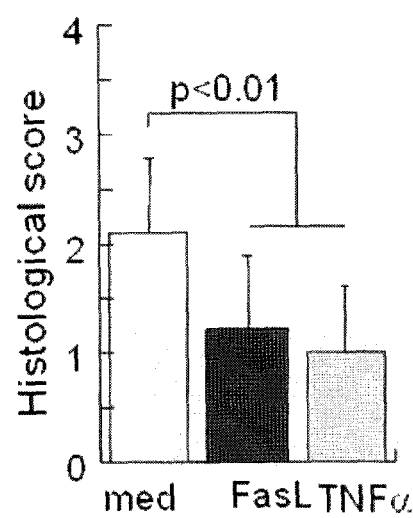
FIG. 7.

Depletion of mPB-Derived T Cells Sensitive to Fas Cross-Linking Ameliorates Graft Versus Host Disease The most significant cause of morbidity in mPB cell transplants is GvHD, a consequence of the intrinsic state of activation of T cells in peripheral blood. To assess the impact of FasL on xenogeneic GvHD, NOD.SCID mice were grafted with $1.5 \times 10^7$ viable mPB from the same unit with and without exposure to the ligand. Preincubation with FasL for 4 hours resulted in survival of all mice, whereas incubation in medium caused death of one third of the recipients (FIG. 7A). Survivors displayed similar levels of human hematopoietic chimerism (FIG. 7B), demonstrating again that SRC within mPB were resistant to Fas-mediated apoptosis. Severe GvHD was the cause of mortality in mice inoculated with mPB incubated in medium, as determined by the severe weight loss (FIG. 7C), clinical score (FIG. 7D) and liver histology (FIG. 7E). Survival and all these features of xenogeneic GvHD were alleviated by brief exposure of mPB cells to FasL. In addition, it is evident from the functional assay that despite apparently similar rates of overall apoptosis, the presence of the ligands affects distinct subsets of lineage-positive mPB cells.

Exposure to Death Ligands Increases Myeloid Progenitor Frequency

Figure 8A:
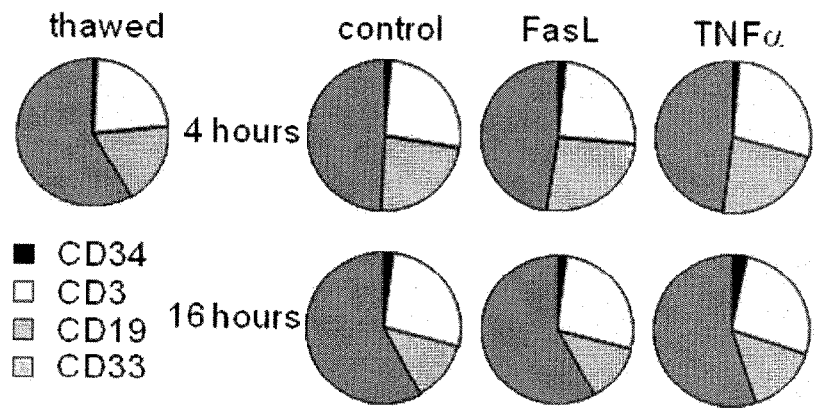
FIG. 8B is a scheme and FIGS. 8A, 8C, 8D and 8E are graphs showing that exposure to death ligands does not impair antigenic stimulation and graft versus tumor reactivity. (A) Cryopreserved mPB were thawed and incubated for 4 or 16 hours with 50 ng/g FasL and 20 ng/g TNF-α. Relative distribution of CD34$^+$ progenitors, T cells (CD3$^+$), B lymphocytes (CD19$^+$) and myeloid cells (CD33$^+$) within the viable cell fraction shows variable sensitivities of these subsets to apoptosis. (B) mPB samples were incubated for 4 or 16 hours with the death ligands, dead cells were eliminated by centrifugation over ficoll and equal numbers of viable cells were plated in semisolid methylcellulose cultures. (C) Clonogenic activity expressed as colony forming cell (CFU) frequency of mPB cells following incubation in medium and with 50 ng/ml FasL or 20 ng/ml TNF-α (n=7-11 in each group). (D) mPB incubated for 4 hours with 50 ng/g FasL were co-incubated with irradiated allogeneic mPB stimulators in mixed lymphocytes reaction (MLR) assays. Proliferation of the responders was determined from CFSE dilution and was quantified using the ModFit software. (E) NOD.SCID mice were inoculated subcutaneously with human colon carcinoma HT29 and infused intravenously with 3×10$^7$ mPB cells preincubated in medium and with FasL for 4 hours. Tumor growth rates, as measured with a caliper according to (mm$^3$=length×width$^2$×0.4), were decreased by infusion of mPB cells irrespective of exposure to FasL.
Figure 8B:
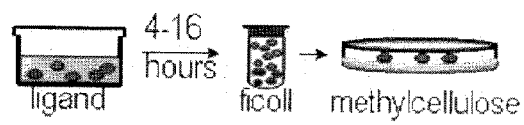
Figure 8C:
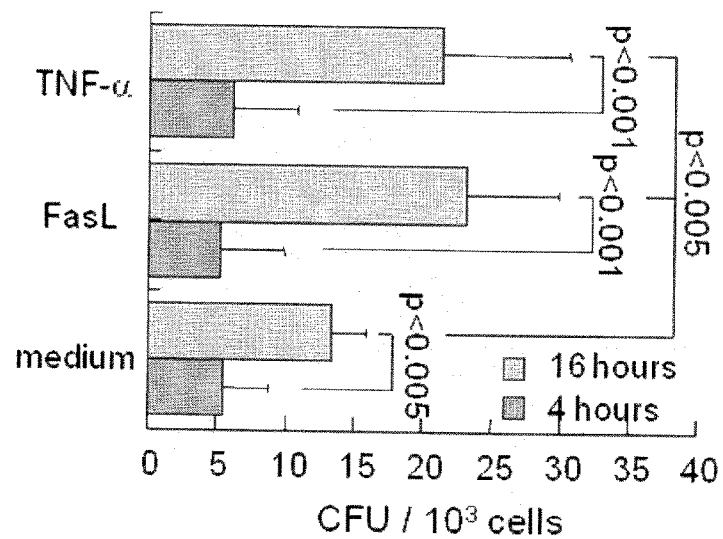

The composition of viable subsets within mPB cultures following brief incubation reflects differential sensitivities of mPB-derived immune cells to apoptosis mediated by the Fas and TNF receptors. The relative distribution of cells is consistent with the high sensitivity of $CD3^+$ T cells to apoptosis during 4 hours of incubation and subsequent death of $CD19^+$ B lymphocytes and $CD33^+$ myeloid cells during longer incubation periods (FIG. 8A). These variations suggested that mPB samples the frequency of progenitors can be increased by brief incubation with the death ligands and elimination of the dead cells (FIG. 8B). Exposure to FasL and TNF-α results in a 4-fold enrichment in myeloid progenitors, doubling the enrichment observed following incubation in medium (FIG. 8C). Similar to UCB cells, exposure to death ligands results in increased CFU frequency, however in variance from UCB cells the period of mPB exposure to the death ligands is much shorter. These data complement the efficiency and safety of the proposed functional elimination of GvHD effectors, showing that the apoptosis-insensitive progenitors are markedly enriched.

Figure 8D:
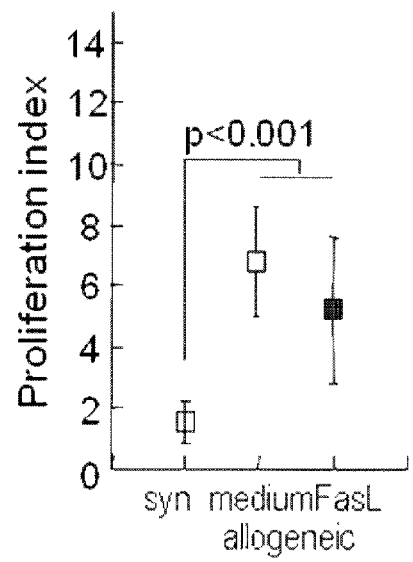
Figure 8E:
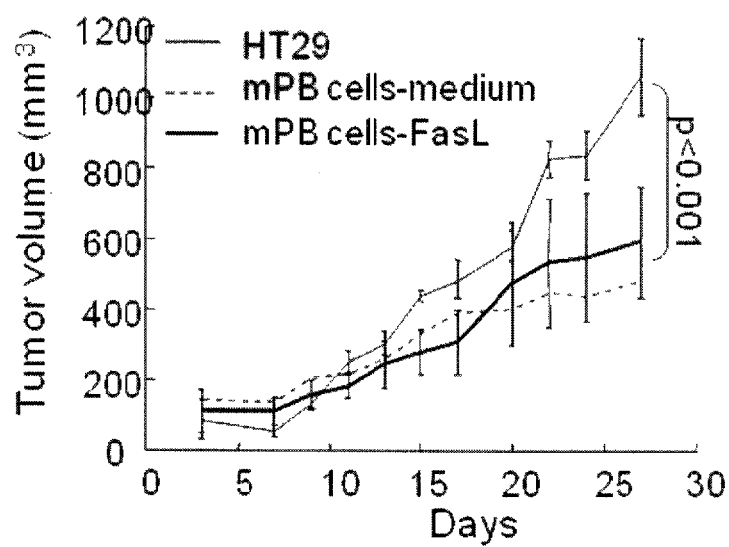

Pretransplant Exposure to FasL does not Impair Immune and Graft Versus Tumor Reactivity The crucial question in experiments using selective T cell depletion to prevent and reduce GvHD severity is whether the graft retains the capacity to elicit potent graft versus tumor reactions. Despite these changes in composition, mPB incubated in medium and with FasL preserve reactivity against irradiated allogeneic human mPB stimulators (FIG. 8D). Consistently, inoculation of mPB with and without exposure to FasL has similar effects on tumor growth suppression in immunocompromised mice bearing subcutaneous HT29 human colon carcinoma tumors (FIG. 8E).

Therefore, unstimulated cryopreserved mPB cells exposed to FasL suppress lethal GvHD, foster engraftment and retain GvT reactivity.

EXAMPLE 3

Pretransplant Depletion of T Cells Prevents Lethal GvHD

Figure 9A:
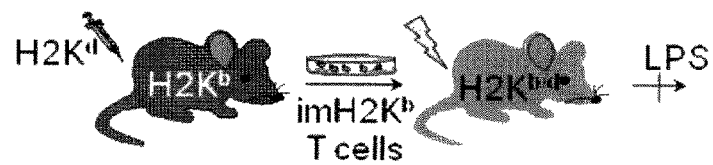
FIGS. 9A and 9E are schemes and FIGS. 9B-9D and 9F-9H are graphs showing that pretransplant depletion of apoptosis-sensitive cells prevents GvHD. (A-D) FasL-mediated elimination of presensitized GvHD effectors. (A) H2K$^b$ mice were immunized twice with $10^7$ H2K$^d$ splenocytes at 3-day intervals. Three days after second immunization splenocytes (imH2K$^b$) were cultured in medium and with 50 ng/ml FasL for 24 hours. (B) Splenocytes harvested from H2K$^d$-immunized H2K$^b$ mice were incubated for 24 hours in medium (n=6) and with 50 ng/ml FasL (n=5). Apoptosis and death were measured from Annexin-V and 7-AAD uptake respectively, in gated CD4$^+$ and CD8$^+$ T cell subsets. (C) Splenocytes of immunized mice display increased responses to the irradiated (3000 rad) allogeneic stimulators (H2K$^d$) as compared to third party stimulators (H2K$^k$). Alloresponses are significantly suppressed by incubation with FasL for 24 hours, while sustaining responsiveness to third party stimuli. Proliferation index was determined from CFSE dilution (n=5 individual incubations). (D) Viable splenocytes (1.5×10$^6$) from the immunized donors were adoptively transferred into sublethally irradiated (650 rad) F1 recipients (H2K$^b$→H2K$^{b/d}$) following ex vivo incubation in medium and with FasL. Differences in survival were polarized by administration of 10 μg lipopolysachariade (LPS) on day +7 (n=8 in each group). (E-H) FasL-mediated depletion of unstimulated donor splenocytes. (E) Sublethally-irradiated (650 rad) F1 recipients (H2K$^{b/d}$) were infused with semiallogeneic splenocytes (H2K$^b$) preincubated for 24 hours in medium and with FasL. (F) Unstimulated splenocytes were incubated for 24 hours in medium (n-7) and with 50 ng/ml FasL (n-9) for measurement of apoptosis in gated CD4$^+$ and CD8$^+$ T cell subsets. (G) Unstimulated splenocytes (H2K$^b$) incubated for 24 hours with and without FasL respond to irradiated allogeneic stimulators (H2K$^d$). (H) Viable splenocytes (1.5×10$^6$) from unstimulated donors were adoptively transferred into sublethally irradiated (650 rad) F1 recipients (H2K$^b$→H2K$^{b/d}$) following ex vivo incubation in medium (n=10) and with FasL (n=10). Mice were challenged with 10 μg LPS (intravenous) on day +7.
Figure 9B:
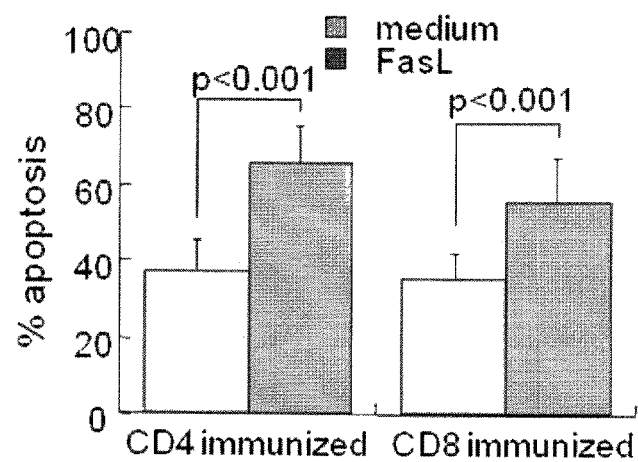
Figure 9C:
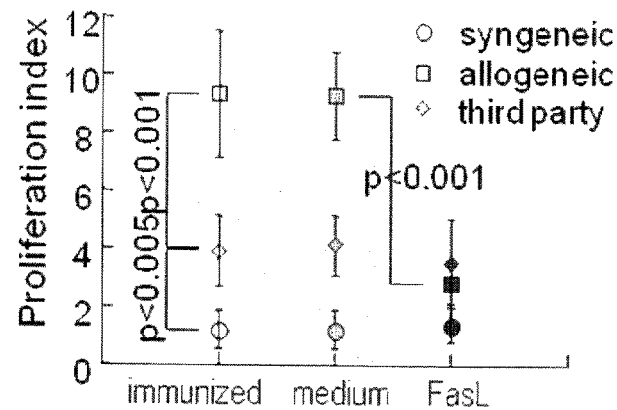

Prevention of Lethal GvHD by Ex vivo Selective Depletion of Host-Sensitized T Cells Both physical depletion of T cells from donor inoculum and FasL-mediated elimination of host-reactive T cells reliably prevent GVHD. Haploidentical murine transplants (parent to child) represent the extreme risk of GvHD, characterized by high levels of mortality. In first stage experiments were recapitulated using depletion of T cells by apoptotic signals following sensitization to host antigens. Antigen-specific sensitization in vitro for 2-3 days causes T cell receptor (TCR)-mediated stimulation of responsive T cells who concomitantly upregulate Fas and its cognate ligand, resulting in execution of the apoptotic cascade in parallel to downregulation of protective antiapoptotic mechanisms. To compare this procedure to tested approach using brief exposure to apoptotic ligands ex vivo without prolonged incubation, the donors were pre-immunized against host antigens in vivo (FIG. 9A). As expected, exposure of the sensitized splenocytes to FasL induced significant apoptosis in both CD4$^+$ and CD8$^+$ T cells (FIG. 9B). The efficacy of sensitization was evident from stronger proliferative responses of lymphocytes harvested from B6 mice (H2K$^b$) immunized with BALB/c lymphocytes (H2K$^d$) against the stimulating H2K$^d$ alloantigens, as compared to third party (H2K$^k$) antigens (FIG. 9C). These responses were sustained following brief (24 hours) incubation of the responders in control medium, however addition of FasL reduced the responsiveness of presensitized splenocytes to H2K$^d$ stimulators. The responses to third party H2K$^k$ antigens were preserved.

Figure 9D:
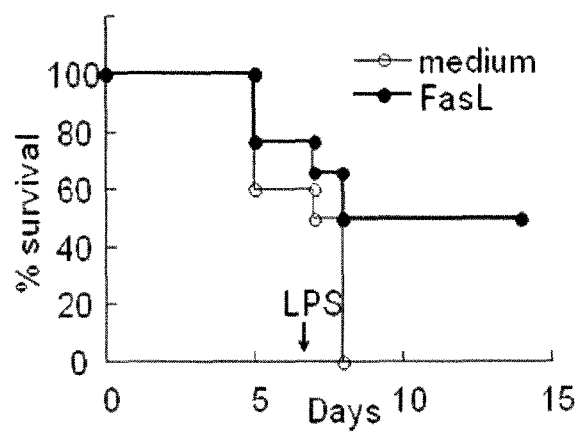

To evaluate the effects of FasL exposure on the ability of sensitized lymphocytes to cause GvHD, viable cells from the H2K$^d$-immunized H2K$^b$ parental donors were adoptively transferred into sublethally irradiated haploidentical F1 recipients (H2K$^b$→H2K$^{b/d}$). Infusion of presensitized splenocytes incubated in control medium caused severe GvHD, which became uniformly lethal following lipopolysacharide (LPS) challenge leading to death of all mice (FIG. 9D). The LPS challenge causes potent immune activation and release of inflammatory cytokines, which exacerbates to maximum ongoing GvHD reactions and precipitates death. By contrast, ex vivo incubation of splenocytes from presensitized donors with FasL prior to infusion led to survival of 50% of mice even after administration of LPS. This in vivo model confirms prior studies showing that alloantigen driven lymphocyte stimulation results in the elaboration of a GVHD-causing population of effector cells that can be specifically eliminated using proapoptotic agents.

Figure 9E:
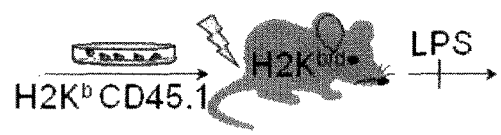
Figure 9F:
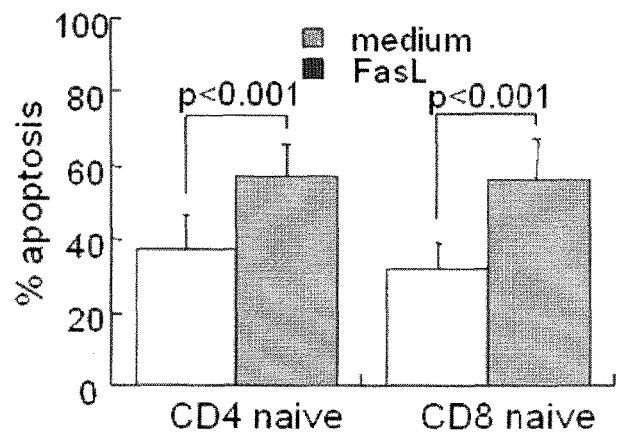
Figure 9G:
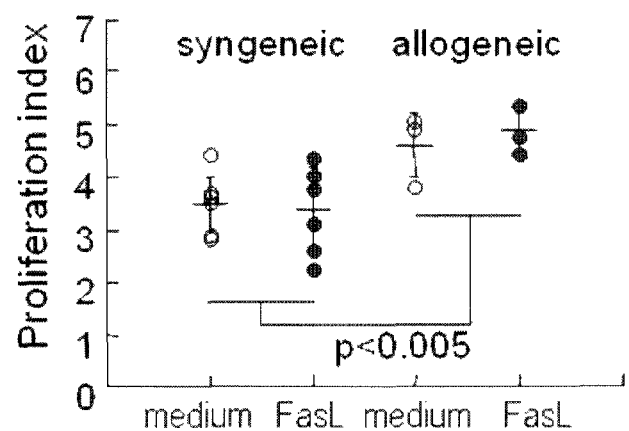

Prevention of Lethal GvHD by Ex vivo Selective Depletion of Unstimulated T Cells We reasoned that pretransplant exposure of donor lymphocytes to host antigens might augment T cell stimulation, and that these alloresponses might persist due to the limited sensitivity of some effector/memory lymphocyte subsets generated in culture to Fas-mediated apoptosis or due to the inability of Fas cross-linking to eliminate completely all the alloreactive T cells. In addition, clinical adaptation of this presensitization approach to human donor:host pairs might be quite challenging. In search for a simpler and more reliable model of FasL selection of alloreactive T cells, the incubation technique was modified to use naïve donor cells that had not been previously exposed to recipient alloantigens (FIG. 9E). In the new approach, naïve splenocytes were depleted ex vivo by exposure to FasL-containing medium in the absence of previous or concurrent exposure to host antigens and in the absence of proliferative stimuli. FasL increased apoptosis of naïve CD4$^+$ and CD8$^+$ T cells (FIG. 9F), however alloresponses were preserved in viable cells subsequently stimulated in vitro (FIG. 9G). Therefore, exposure of unstimulated splenocytes to FasL preserves the capacity of apoptosis-insensitive cells to respond to allogeneic antigens.

Figure 9H:
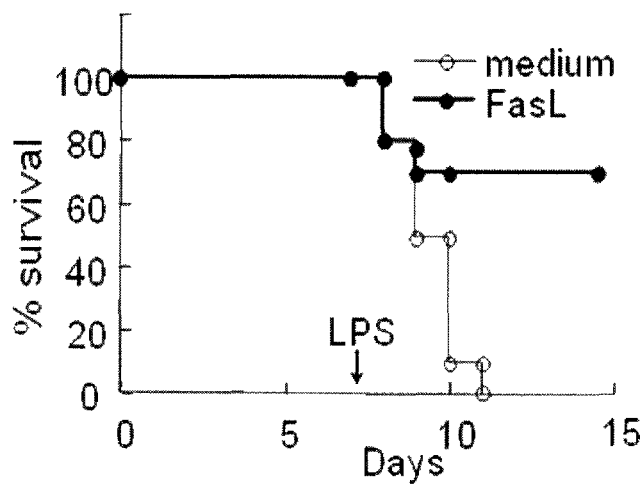

To assess the effect of ex vivo elimination of unstimulated lymphocytes, viable splenocytes were infused into sublethally irradiated haploidentical F1 recipients (H2K$^b$-GFP→H2K$^{b/d}$). Unsensitized lymphocytes incubated in medium were less potent mediators of lethal GvHD, therefore LPS was used to induce cytokine storm and polarize the activity of donor lymphocytes. Survival of 70% of recipients of FasL-pretreated unstimulated splenocytes following the LPS challenge was superior to survival of recipients of ex vivo depleted host-stimulated splenocytes, whereas lethal GvHD was precipitated in all recipients of splenocytes incubated in control medium (FIG. 9H). Thus, treatment of donor lymphocytes with FasL prevented lethal GvHD (including LPS challenge) in a high-risk parent to F1 hybrid acute GVHD model in the absence of previous exposure to host antigens.

Quantitative and Qualitative Aspects of GvHD Prevention

Figure 10A:
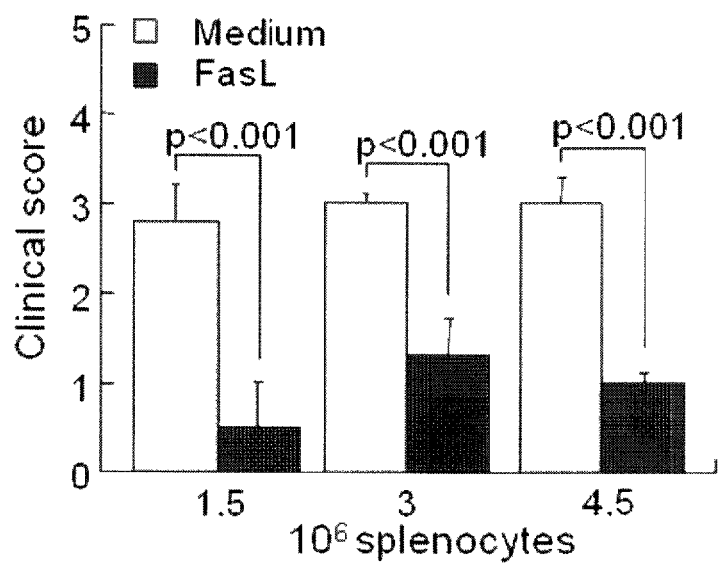
FIGS. 10A-10E are graphs showing that Fas-mediated depletion of unstimulated splenocytes decreases GvHD activity of haploidentical and allogeneic immune cells. Sublethally-irradiated (650 rad) F1 recipients (H2K$^{b/d}$) were infused with various numbers (1.5-4.5×10$^6$) of semi-allogeneic splenocytes preincubated for 24 hours in medium and with FasL. (A) Recipients of splenocytes incubated with and without FasL were scored clinically according to normal (0) and abnormal (1) parameters: 1. skin disease and hair loss, 2. weakness, 3. footpad hyperkeratosis and 4. diarrhea. (B) Weight loss in recipients of various numbers of donor splenocytes incubated with and without FasL (n=5-10 in each group). (C-D) Haploidentical transplants of 3×10$^6$ splenocytes were compared to allogeneic transplants (H2K$^b$→H2K$^d$) following incubation with and without FasL for 24 hours (n=6-10 in each group). The clinical score (C) and weight loss (D) were measured after one week. (E) Splenic contents of T and B lymphocytes decreases gradually during the first week after irradiation (n=5 in each group). Survivors of the lipopolysacharide (LPS) challenge display marked stimulation of these subsets (2 days after LPS infusion), which is blunted by pretreatment of unstimulated splenocytes with FasL (n=7).
Figure 10B:
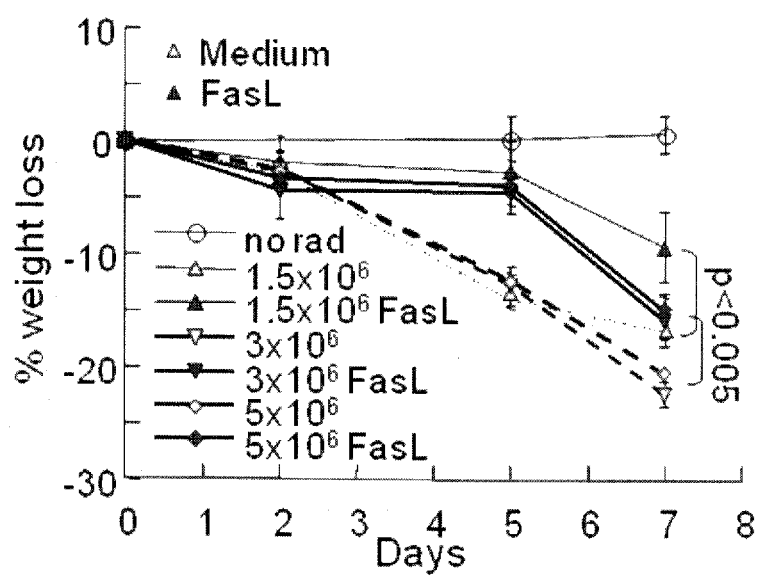
Figure 10C:
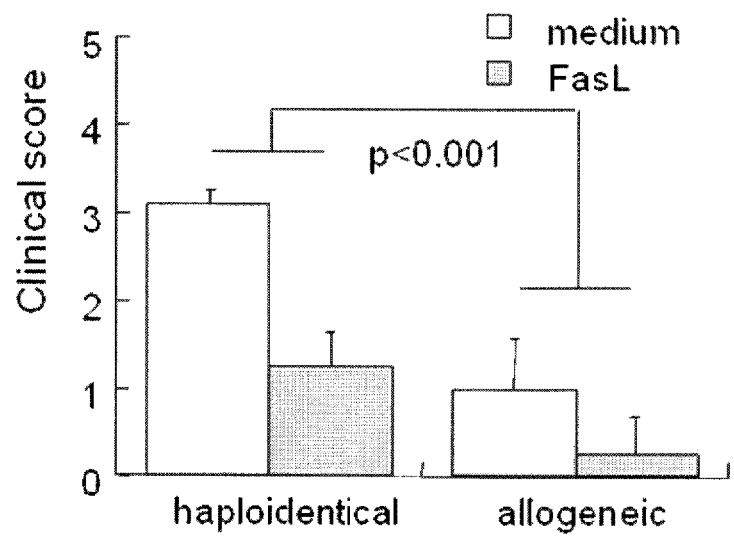
Figure 10D:
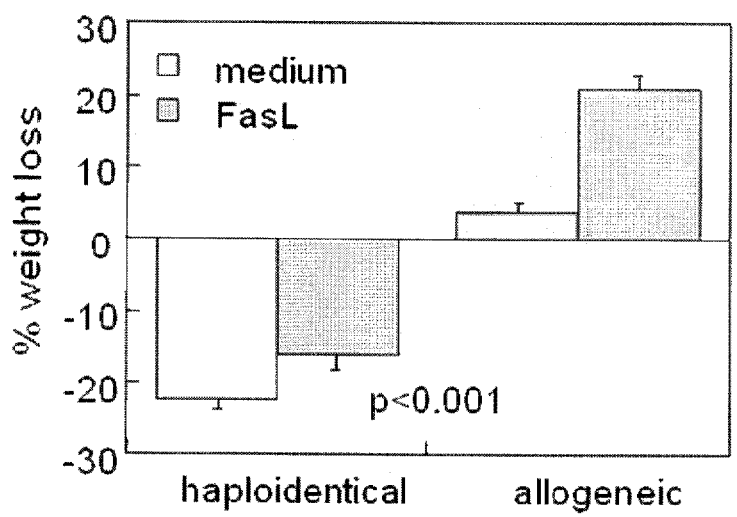

Adoptive transfer of viable splenocytes after incubation in control medium caused significant GvHD in sublethally irradiated haploidentical F1 recipients, which was blunted by donor cell preincubation with FasL (FIG. 10A). The dose-dependent decrease in body weight is evidence of progressive GVHD severity in recipients of haploidentical splenocytes incubated in medium (FIG. 10B). By contrast, weight loss was significantly reduced in F1 hybrid mice infused with naïve parental splenocytes that had been preincubated with FasL, consistent with amelioration of GvHD severity. The clinical GvHD score (FIG. 10C) and weight loss (FIG. 10D) in haploidentical transplants (H2K$^b$→H2K$^{b/d}$) exceeded those observed in allogeneic mouse combinations (H2K$^b$→H2K$^d$), and consistently the protective effect of preincubation with FasL was more effective in GvHD prevention in allogeneic transplants. Notably, adoptive transfer of 1.5-5×10$^6$ T cells in mice is equivalent to doses of 60-200×10$^6$ T-cells/kg in humans, whereas threshold safety for prevention of GvHD by phenotypic T cell depletion is 0.02×10$^6$ T-cells/kg in haploidentical transplants.

Figure 10E:
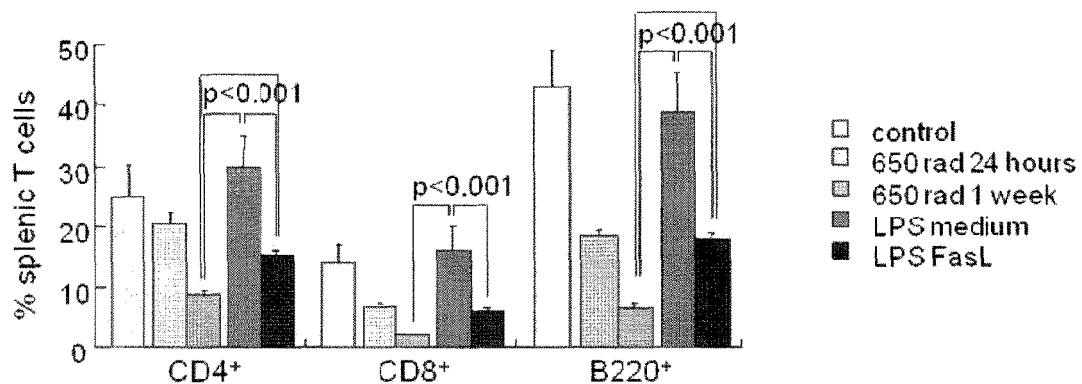

To evaluate the differences in immune profiles of survivors in the different experimental groups, the composition of the spleens was assessed before and 2 days after the LPS challenge (FIG. 10E). All T and B cell subsets decreased during the first week following sublethal irradiation, irrespective of adoptive transfer of splenocytes. Recipients of lymphocytes incubated in control medium responded to LPS by a surge in splenic CD4$^+$ and CD8$^+$ T cells and B lymphocytes (p<0.001), which were significantly attenuated in recipients of FasL-pretreated splenocytes (p<0.001). Repetition of these experiments using purified T cells as opposed to unfractionated splenocytes showed similar results (data not shown).

Figure 11A:
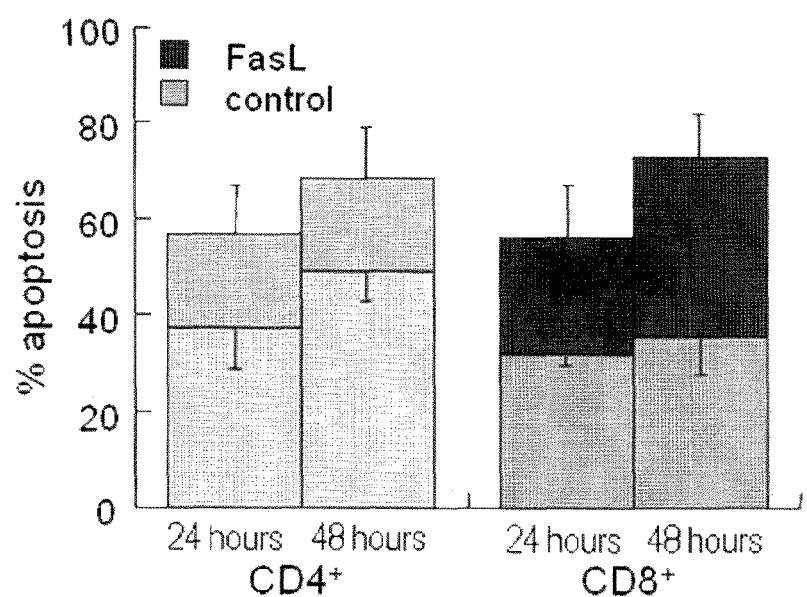
FIG. 11C is a scheme and FIGS. 11A, 11B and 11D-F are graphs showing that Fas cross-linking ameliorates GvHD in NOD.SCID mice. (A) Splenocytes incubated in medium and with 50 ng/ml FasL display variable levels of spontaneous (light bars) and Fas-mediated apoptosis (dark bars). Apoptosis was measured by Annexin-V uptake on gated CD4$^+$ and CD8$^+$ T cells subsets after 24 and 48 hours of incubation (n=7-9). (B) Fractional distribution of viable CD4$^+$ and CD8$^+$ T cells, CD4$^+$ CD25$^+$ regulatory T cells and B lymphocytes (B220$^+$) before and after 48 hours of incubation in medium and with FasL. (C) Splenocytes from C57BL/6 donors incubated in medium and with 50 ng/ml FasL were infused into allogeneic NOD.SCID mice (H2K$^b$→H2K$^{g7}$): 3×10$^6$ and 10$^7$ naïve splenocytes preincubated for 24 and 48 hours, respectively. (D) Survival of NOD.SCID mice infused with splenocytes preincubated in control medium (n=9) and with 50 ng/ml FasL (n=10). Lethal GvHD was precipitated by intravenous injection of 10 μg LPS. Mice were evaluated after 3 weeks for clinical score with incidence of gastrointestinal involvement (GI) (E), and weight loss (F).
Figure 11B:
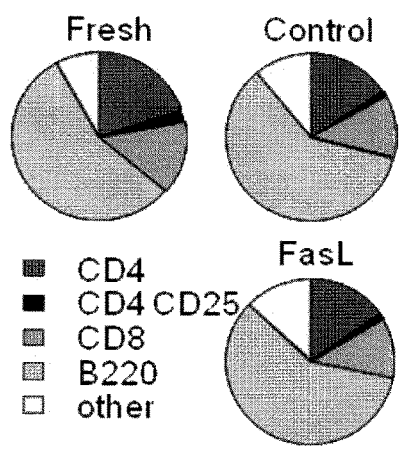

Simulation of GvHD in NOD.SCID Mice to Determine the Time of Exposure to Death Ligands Ex vivo Prevention of GvHD by selective depletion of unstimulated donor T cells questions the involvement of two possible mechanisms. First, partial immuno and myelodepletion induced by sublethal irradiation suggests that residual host immune elements might operate successfully against FasL-deleted donor T cells, resulting in suppression of GvHD. Second, conditioning with total body irradiation induces tissue injury that plays an important role in the afferent arm of GvHD. To assess both these mechanisms, the disease was induced in lymphocyte-deficient NOD.SCID mice without pretransplant conditioning. Exposure of unstimulated splenocytes to FasL for 24 and 48 hours elicited significant apoptosis (FIG. 11A), with corresponding decrease in fractions of $CD4^+$ and $CD8^+$ viable T cells (FIG. 11B).

Figure 11C:
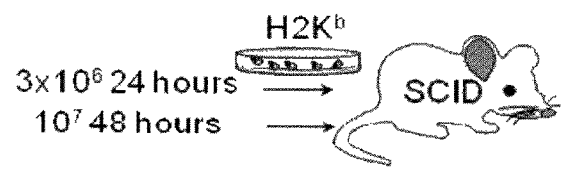
Figure 11D:
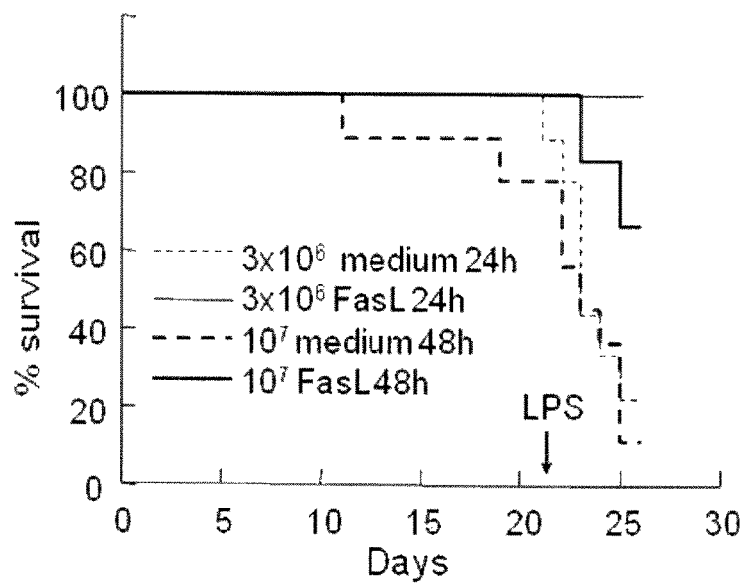
Figure 11E:
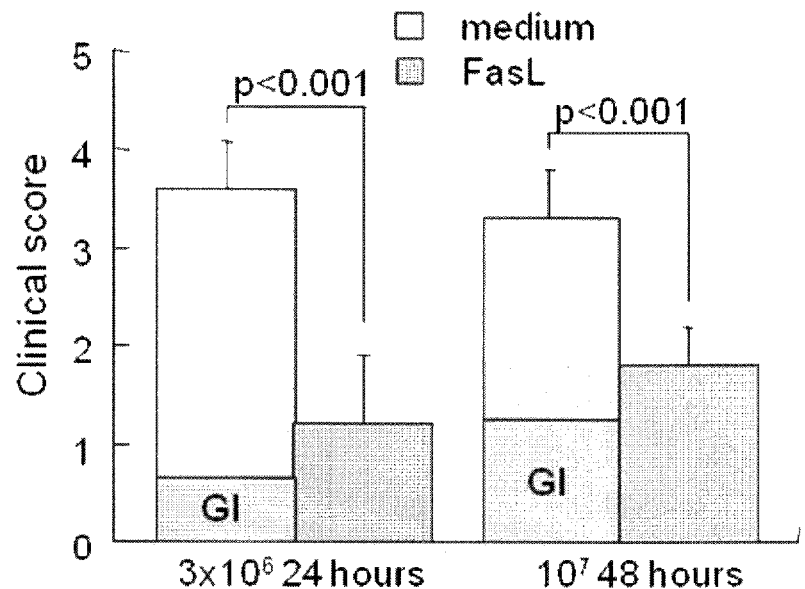
Figure 11F:
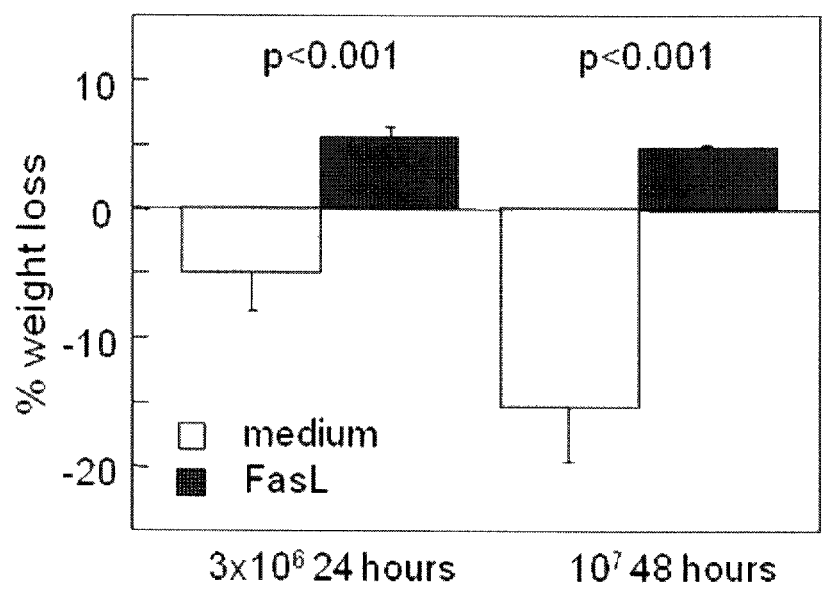

Following a series of calibration experiments, NOD.SCID mice were infused with $3 \times 10^6$ or $10^7$ naïve allogeneic splenocytes ($H2K^b \rightarrow H2K^{g7}$) after 24 or 48 hours of ex vivo incubation in FasL-containing medium, respectively (FIG. 11C). Infusion of splenocytes incubated in medium caused ~20% mortality at the higher dose, and severe mortality was recorded after administration of the LPS challenge (FIG. 11D). The protective effects of FasL incubation on donor lymphocyte-mediated lethal GvHD were again highlighted by superior survival of mice following LPS injection (FIG. 11D). This protective effect was accompanied by remarkable improvement in clinical score (FIG. 11E)) and weight loss (FIG. 11F). Prevention of GvHD in NOD.SCID mice in the absence of competent residual host immunity and without predisposing host factors such as conditioning-induced tissue injury emphasizes that GvHD is primarily a consequence of modulation of donor T cell inoculum by exposure of unstimulated lymphocytes to FasL.

EXAMPLE 4

Figure 12A:
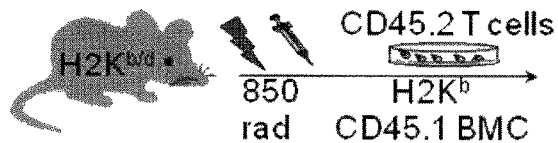
FIG. 12A is a scheme.
Figure 12B:
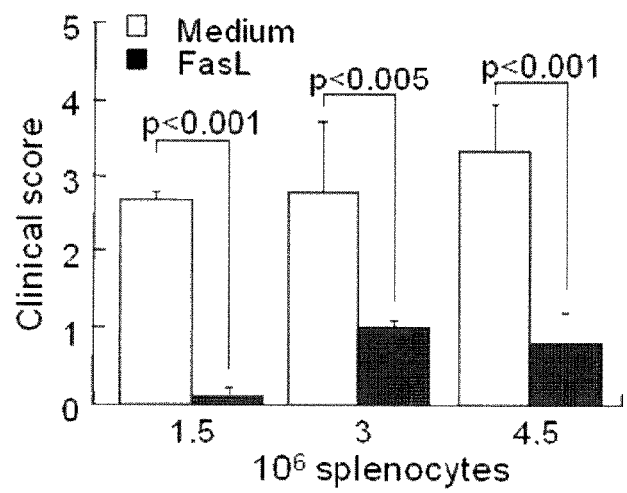
FIGS. 12B-C are graphs and FIG. 12D is a picture and a graph showing elimination of Fas-sensitive naïve immune cells in haploidentical bone marrow transplants. (A) F1 recipients (H2K$^{b/d}$) irradiated at 850 rad were grafted with 5×10$^6$ BMC (H2K$^b$, CD45.1) and various numbers of donor splenocytes (H2K$^b$, CD45.2, GFP). Recipients of splenocytes incubated in medium and with FasL for 48 hours (n=8 in each group) were assessed for clinical score (B) with incidence of gastrointestinal involvement (GI) and weight loss (C) at 3 weeks post-transplantation. (D) At 3 weeks post-transplantation the mice were sacrificed for histological evaluation of skin and liver in recipients of 3×10$^6$ splenocytes incubated in medium and with FasL (n=5): 0-no infiltration, 1-scarce infiltrates, 2-patchy infiltration, 3-diffuse infiltration, 4-deterioration of tissue infrastructure.
Figure 12C:
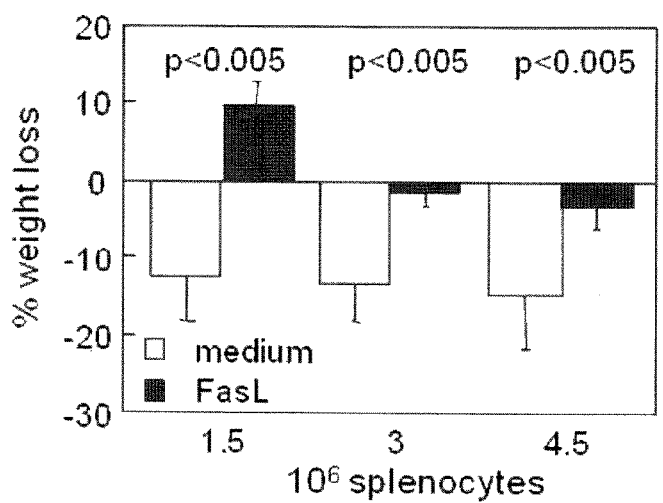
Figure 12D:
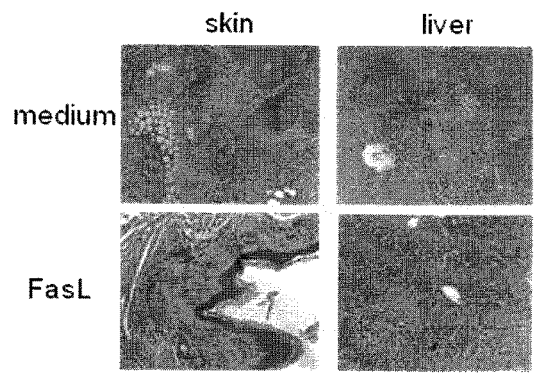
Figure 12E:
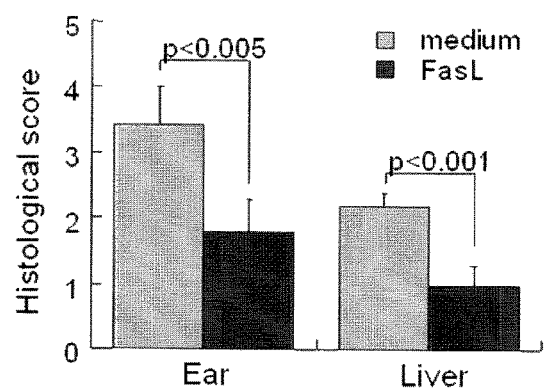
FIG. 12.

The Impact of Ex vivo Selective Depletion of Unstimulated Lymphocytes on Hematopoietic Cell Engraftment Depletion of Fas-Sensitive Naïve Splenocytes Alleviates GVHD in Bone Marrow Transplants To extend the findings of the GvH-like model to the transplant setting, the effect of Fas-mediated depletion of host-naïve cells was assessed in mice undergoing haploidentical BMT together with donor lymphocyte infusion (FIG. 12A). Irradiated F1 recipients that received $5 \times 10^6$ haploidentical BMC together with 1.5, 3 and 4.5 million splenocytes preincubated in control medium ($H2K^b \rightarrow H2K^{b/d}$) manifest severe GvHD (FIG. 12B) and significant 10-15% weight loss (FIG. 12C). The clinical score of GvHD was corroborated by histological analysis of ear skin and liver specimens (FIG. 12D). Preincubation of the infused naïve splenocytes with FasL for 24 hours decreased the clinical GvHD score ($p<0.005$) blunted weight loss ($p<0.005$) and reduced lymphocytic infiltrates in the affected target organs ($p<0.005$). Residual low-grade GvHD activity did however persist after infusion of $3-4.5 \times 10^6$ FasL-pretreated haploidentical splenocytes. It is noteworthy that this dose of T cells corresponds to doses of $4-6 \times 10^7$ T cells/Kg, numbers of T-cells often administered in unmanipulated allogeneic whole bone marrow transplants from matched unrelated donors.

Figure 13A:
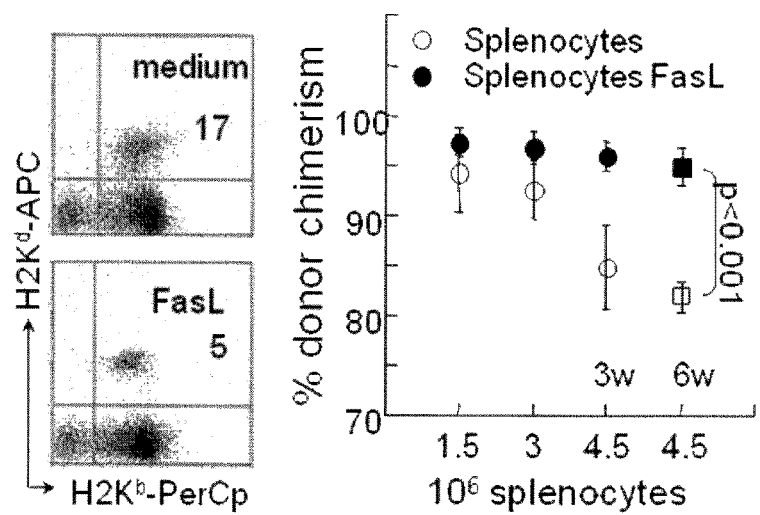
FIG. 13A is a graph and FACS scan.

Immuno-Hematopoietic Reconstitution Following Haploidentical BMT and Selective Depletion of Apoptosis-Sensitive Cells GvHD depresses graft function and profoundly abrogates recipient immune responses. To determine how depletion of Fas-sensitive donor splenocytes affects immuno-hematopoietic reconstitution following transplantation, hosts were assessed for survival of the grafted donor lymphocytes, chimerism and immune responsiveness to unrelated antigens. Recipients of the highest dose ($4.5 \times 10^6$) of unmanipulated donor splenocytes preincubated in control medium displayed decreased levels of chimerism at 3 weeks and 6 weeks post-transplantation (FIG. 13A), as compared to recipients of FasL pretreated splenocytes, demonstrating that pre-treatment of donor lymphocytes abrogated the graft suppressive effects of the untreated cells.

Figure 13B:
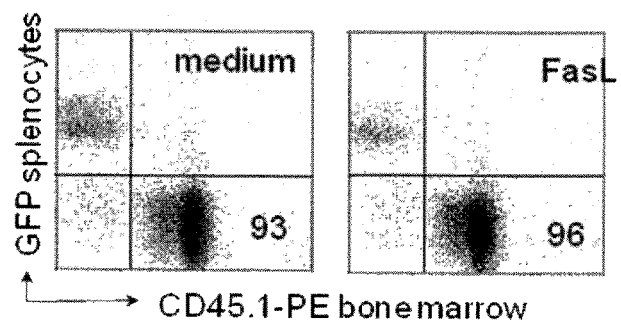
FIGS. 13B and 13D are FACS scans and FIG. 13C is a graph showing immune reconstitution after selective depletion of Fas-sensitive naïve immune cells in haploidentical bone marrow transplants. (A) F1 recipients (H2K$^{b/d}$) irradiated at 850 rad were grafted with 5×10$^6$ BMC (H2K$^b$, CD45.1) and various numbers of donor splenocytes (H2K$^b$, CD45.2, GFP). Donor (H2K$^b$) and host (H2K$^{b/d}$) chimerism was determine in peripheral blood at 3 weeks post-transplantation (n=5). The mice were sacrificed at 3 weeks post-transplantation to determine: (B) The major contribution to spleen reconstitution was from the bone marrow (CD45.1, GFP$^+$) with few of the infused splenocytes being present at this time point (CD45.2, GFP$^+$). Data are representative of 5 independent measurements. (C) Responses to third party (H2K$^k$) irradiated stimulators (at 1:3 responders:stimulators ratio) in MLR assays. Proliferation was determined from CFSE dilution in recipients of unstimulated splenocytes incubated in medium and with FasL (n=4). (D) GFP$^+$ donor splenocytes in mesenteric lymph nodes at 24 hours after transplantation into sublethally irradiated (650 rad) wild type recipients. Data are representative of 4 independent measurements.
Figure 13C:
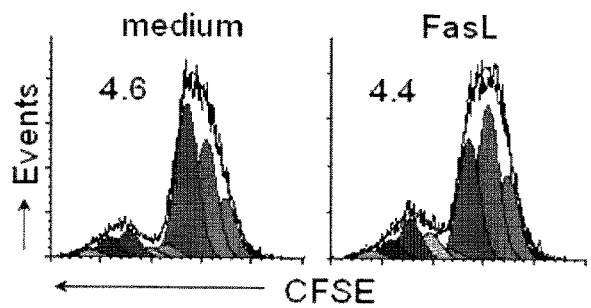

Because the mature lymphocytes that were infused at the time of transplantation compete with lymphocytes generated by the bone marrow graft for peripheral homeostatic expansion and effect the net lymphocyte numbers, the impact of FasL treated lymphocyte infusions on lymphoid reconstitution was examined. Minor CD45 antigen disparity (CD45.1 vs. CD45.2) were used to differentiate between infused splenocytes and BMC graft-derived T cells in the recipients during the weeks following transplant. Despite the fact that F1 recipients do not reject parental immune cells, few of the infused splenocytes ($H2K^b$, $CD45.2^+GFP^+$) were detected in peripheral lymphoid organs of the recipients at 3 weeks post-transplantation, whether or not they had been incubated with FasL or in control medium (FIG. 13B). Qualitatively, recipients of control and FasL-pretreated splenocytes displayed unresponsiveness to both donor and host antigens as expected for chimeric mice, and responded equally well to third party ($H2K^k$) antigens (FIG. 13C). Therefore, ex vivo treatment of lymphocytes with FasL seems to effect neither quantitative nor functional immune reconstitution after transplantation, yet prevention of GvHD improves donor cell engraftment.

Figure 13D:
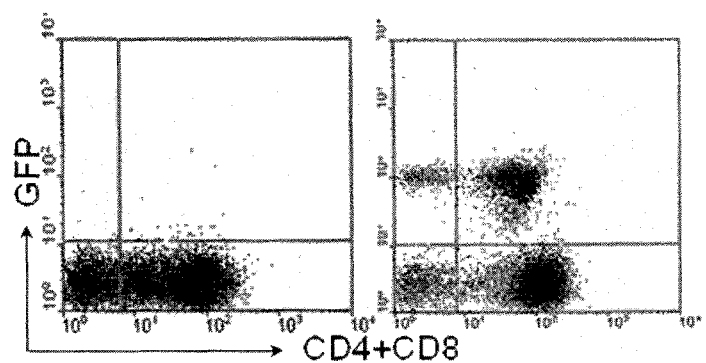

We questioned whether prevention of GvHD by preincubation of unstimulated lymphocytes with FasL is caused by impaired navigation capacity of the cells. This possibility was assessed by infusion of viable splenocytes into sublethally irradiated F1 recipients ($H2K^b$-GFP$\rightarrow H2K^{b/d}$) and demonstration that lymphocytes homed to recipient spleen and mesenteric lymph nodes 24 hours after infusion, whether the cells had been preexposed to FasL or to control medium (FIG. 13D). These data demonstrate that preexposure of lymphocytes depletes potential GvHD effectors without impairing their navigation ability.

Exposure of Hematopoietic Cells to Death Ligands Improves Engraftment

Figure 14A:
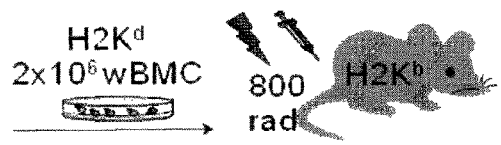
FIGS. 14A, 14C and 14E are schemes
Figure 14B:
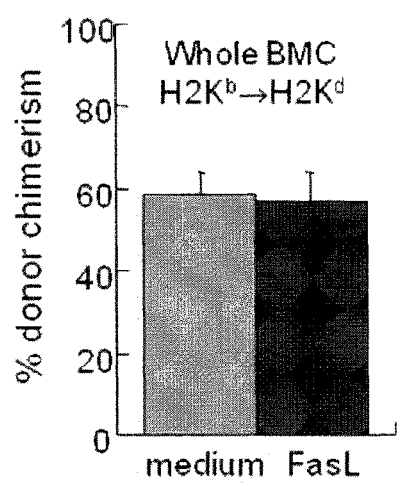
FIGS. 14B, 14D and 14F are graphs showing that FasL-mediated depletion of unstimulated lymphocytes support hematopoietic cell engraftment. (A) Whole bone marrow cells (wBMC) were incubated for 24 hours with and without 50 ng/ml FasL and 2×10$^6$ cells were grafted into sublethally irradiated (800 rad) allogeneic hosts (H2K$^d$→H2K$^b$). (B) Peripheral blood chimerism at 3 weeks was not affected by preincubation with FasL (n=6). (C) Transplantation of 10$^6$ lineage-negative BMC (n=7) into irradiated (800 rad) allogeneic hosts (H2K$^d$→H2K$^b$) was supplemented with 10$^6$ splenocytes from F1 donors (H2K$^{b/d}$) devoid of GvHD activity after preincubation in medium (n=5) and with FasL (n=6) for 24 hours. (D) Addition of splenocytes improved hematopoietic cell engraftment irrespective of exposure to FasL. (E) Mixed chimerism was induced by transplantation of 5×10$^5$ lin$^-$ BMC into allogeneic recipients (H2K$^d$→H2K$^b$) irradiated at 750 rad (control, n=6). After 10 days the mice were infused with allogeneic (H2K$^d$) 10$^6$ lymphocytes (DLI). (F) The levels of donor chimerism increased 3 weeks after DLI preincubated for 24 hours in medium and with FasL (n=6), as compared to mice that did not receive lymphocyte infusion (control).
Figure 14C:
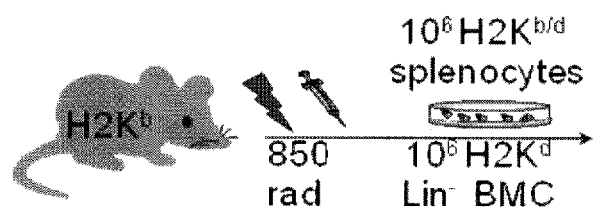
Figure 14D:
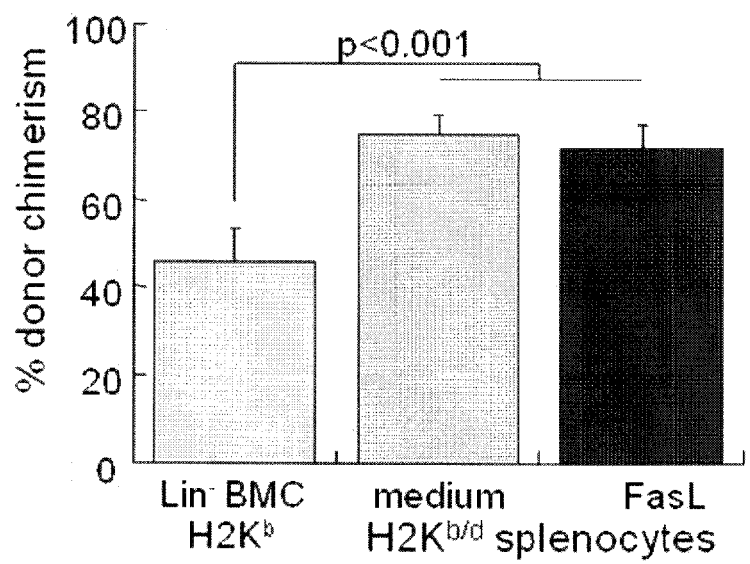
Figure 14E:
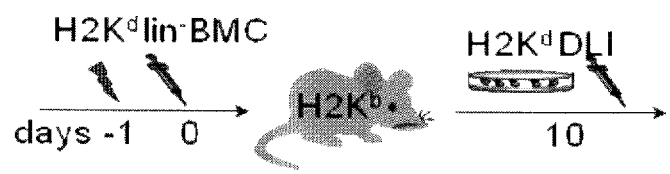

Depletion of all T cells from the hematopoietic grafts removes engraftment-facilitating cells, requiring a compensatory infusion of large doses of stem cells. Preincubation of the graft with FasL for 24 hours (FIG. 14A) did not affect the levels of donor chimerism induced by transplantation of $2 \times 10^6$ allogeneic ($H2K^d \rightarrow H2K^b$) whole BMC into irradiated hosts (FIG. 14B). Therefore, engraftment is not lost when heterogeneous whole BMC populations are exposed to death ligands before transplantation.

T cells support hematopoietic progenitor engraftment through two mechanisms: a) donor T cells may counteract graft rejection by residual donor immunity, and b) T cells co-reside with progenitors at sites of seeding in the bone marrow and support engraftment through unidentified non-immunogenic mechanisms. To determine whether depletion of apoptosis-sensitive T cells to prevent rejection also eliminates engraftment-facilitating cells, irradiated H2K$^b$ mice were grafted with 10$^6$ viable unmanipulated H2K$^d$ lin$^-$ progenitors. In this model splenocytes from F1 donors (H2K$^{b/d}$), which are devoid of GvHD activity were used. Infusion of 10$^6$ viable F1 splenocytes after incubation in control medium or with FasL increased the levels of donor chimerism (FIG. 14C), demonstrating that depletion of Fas-sensitive splenocytes does not eliminate cells that facilitate HSPC engraftment.

Figure 14F:
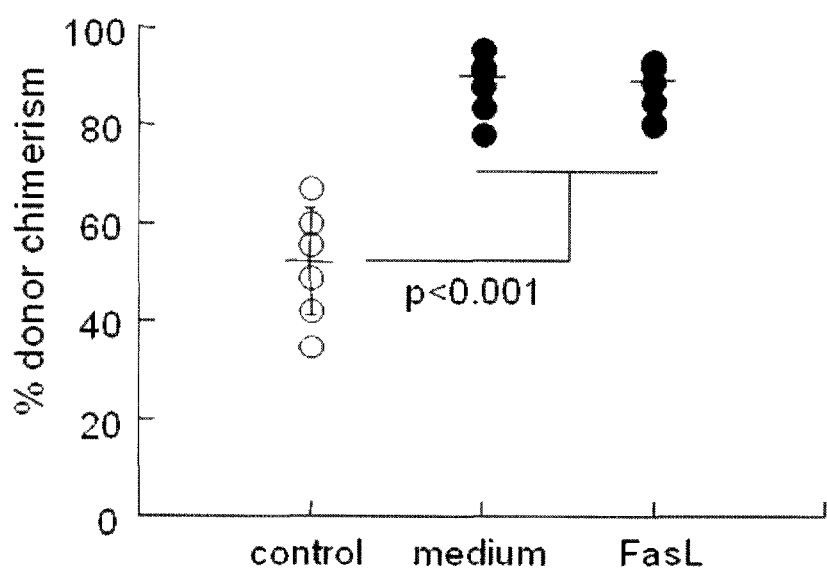

Preexposure of Donor Lymphocytes to Death Ligands Preserves the Engraftment-Supporting Activity of Delayed Donor Lymphocyte Infusion Post-transplant infusion of donor lymphocytes (DLI) is an effective approach to improve donor chimerism, enhance responsiveness to infections and foster graft versus tumor reactions. Although delayed DLI is better tolerated and causes less GvHD than infusion of lymphocytes in conditioned recipients at the time of hematopoietic transplantation, the lymphocytes have the capacity to increase the severity of GvHD. Delayed donor lymphocyte infusion in a model of mixed chimerism (FIG. 14E) was effective in increasing the levels of donor chimerism irrespective of pretransplant exposure of the lymphocytes to FasL (FIG. 14F). Therefore, depletion of Fas-sensitive unstimulated lymphocytes does not impair the efficacy of post-transplant DLI.

FasL Alleviates GVHD without Impairing GVT

The overall success of stem cell transplantation performed for the treatment of malignant disease may depend on graft versus tumor (GvT) effects. Bulk depletion of T cells (either ex vivo or by administration of potent in vivo immune suppression) can blunt the GvT effect and increase post-transplant relapse rates in a variety of clinical situations. It was examined whether FasL incubations abrogated GvT effects in parallel to its salutary effect on GvHD in two experimental models. In a first model the preservation of GvT reactivity of host-matched lymphocytes after FasL-mediated depletion against an allogeneic tumor was assessed. CT26 colon carcinoma cells (H2K$^d$) were implanted in NOD.SCID mice (H2K$^{g7}$) adoptively transferred with 1.5×10$^7$ splenocytes from NOD (immunocompetent) donors (H2K$^{g7}$, FIG. 15A). Splenocytes preincubated with FasL for 24 hours suppressed the growth of tumor implants to a similar degree as compared with splenocytes incubated in control medium (FIG. 15B), confirming that incubation with FasL preserves lymphocyte-mediated GvT reactivity. In the second model H2K$^a$ mice bearing MHC-matched neuroblastoma (Neuro-2a, H2K$^a$) tumors were sublethally irradiated and grafted with 2×10$^6$ lin$^-$ progenitors from allogeneic donors (H2K$^b$, FIG. 15C). Infusion of lymphocytes from F1 donor (H2K$^{b/d}$), which recognize the tumor as self, had no significant impact on tumor growth (FIG. 15D). In variance, infusion of allogeneic splenocytes (H2K$^b$) reduced tumor growth rates, however 80% of the mice died within 3 weeks because of severe GvHD. Ex vivo Fas-mediated depletion of unstimulated donor splenocytes (H2K$^b$) showed equal tumor-suppression effect while alleviating lethal GvHD, and all mice survived to the experimental end point. These data confirm that GVHD is not a prerequisite for GvT effects, therefore prevention of GvHD does not impair anti-tumor activity of selectively-depleted lymphocytes.

FasL-Mediated Purging of Malignant Cells

Despite the significant advantages and safety of autologous transplants after aggressive radiochemotherapy, contamination of the graft with residual malignant cells is a risk factor of disease relapse. To evaluate this possibility, mice were infused with a mixture of bone marrow cells and A20 B cell lymphoma, at a dose that is lethal in syngeneic BALB/c mice (FIG. 15E). Whereas infusion of cell mixtures incubated in medium resulted in death of 80% of the recipients within 4 weeks, all mice infused with grafts exposed to FasL survived this period (FIG. 15F). These data document the efficacy of short incubation with death ligands for depletion of apoptosis-sensitive malignant cells from the hematopoietic graft.

Figure 15G:
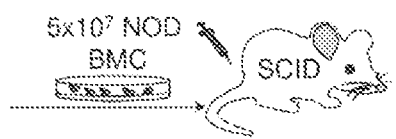
Figure 15H:
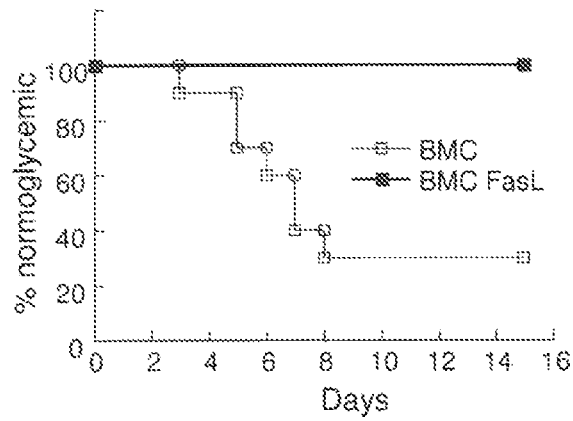

Depletion of Fas-Sensitive Cells Prevents Adoptive Transfer of Autoimmunity in Autologous Transplants Type 1 diabetes is an autoimmune reaction that destroys the insulin-producing β-cells in the pancreatic islets of Langerhans. This disorder is generally modeled in non-obese diabetic mice (NOD), with a disease incidence above 80% in females aged 30 weeks. Autoimmune diabetes is adoptively transferred by T cells, but not so efficient by transplantation of whole bone marrow cells. Preliminary experiments determined that 5×10$^7$ bone marrow cells transfer the disease into ~50% of sublethally-irradiated NOD.SCID mice (FIG. 15G), both strains bearing the same haplotype (H2K$^{g7}$). In addition, NOD.SCID mice do not reject the donor cells since they lack competent T and B lymphocytes. Whereas adoptive transfer of BMC incubated in medium for 48 hours transferred the disease effectively, non of the recipients of BMC exposed to FasL displayed hyperglycemia (FIG. 15H). Therefore, exposure of hematopoietic cells to death ligands ex vivo eliminates cells with autoimmune reactivity.

---

The invention claimed is:

1. A device, comprising: a container comprised of a biocompatible material and a biologically active apoptosis-inducing ligand immobilized to a surface, wherein said device is adapted for cell selection by apoptosis of apoptosis-sensitive cells and said apoptosis-inducing ligand is a single agent selected from the group consisting of tumor necrosis factor α (TNF-α), Fas ligand (FasL), Trail or Tweak.

2. The device of claim 1, wherein said surface is the inner surface of said container.

3. The device of claim 1, wherein said container is selected from the group consisting of a bag, a column, a tube, a bottle, a vial, and a flask.

4. The device of claim 1, wherein said biocompatible material is selected from the group consisting of polypropylene, polystyrene, silicone, polyvinyl chloride, and a combination thereof.

5. The device of claim 1, wherein said immobilized apoptosis-inducing ligand is Fas ligand (FasL).

6. The device of claim 1, wherein said surface is the surface of beads present within said container.

7. A cell selection kit, comprising: (a) a device of claim 1; and (b) a solution for maintaining the integrity and activity of said apoptosis-inducing ligand within said device.

8. The kit of claim 7, further comprising a second apoptosis-inducing ligand.

9. A method for selecting an apoptosis-signaling resistant cell from a cell population, said cell population comprises an apoptosis-signaling resistant cell and an apoptosis-signaling sensitive cell, said method comprising the steps of:
(a) introducing a sample comprising a cell population into the device of claim 1; and
(b) incubating said cells within said device;
thereby selecting for apoptosis-signaling resistant cells through enrichment of such apoptosis-signaling resistant cells in the cell population by inducing cell death in apoptosis-signaling sensitive cells to eliminate such apoptosis-signaling sensitive cells from the cell population.

10. The method of claim 9, wherein said apoptosis-signaling resistant cell comprises: a stem cell, an immune cell insensitive to activation-induced cell death (AICD), a progenitor cell, or any combination thereof.

11. The method of claim 10, wherein said stem cell is a bone marrow stem cell.

12. The method of claim 10, wherein said immune cell insensitive to activation-induced cell death is a T cell.

13. The method of claim 9, wherein said cell population is derived from: bone marrow, a progenitor cell, mobilized peripheral blood, or umbilical cord blood (UCB).

14. A method for improving the clinical outcome of hematopoietic stem and progenitor cells (HSPC) transplantation, comprising the steps of:
(a) providing a sample comprising a cell population, said cell population comprises stem and progenitor cell;
(b) contacting said cell population with a biologically active apoptosis-inducing ligand, Fas ligand (FasL) for a period of 1 to 24 hours or tumor necrosis factor α (TNF-α) for a period of 24 to 48 hours, in the device of claim 1;
(c) retrieving the cells of step (b); and
(d) transplanting the cells of step (c);
thereby improving the clinical outcome of hematopoietic stem and progenitor cells (HSPC) transplantation.

15. A method for eliminating a malignant cell in a composition comprising a progenitor-cell transplant, comprising the steps of:
(a) providing a composition comprising a progenitor-cell transplant; and
(b) contacting said composition with an apoptosis-inducing ligand for a period of about 24 hours in the device of claim 1;
thereby, eliminating a malignant cell in a composition comprising a progenitor-cell transplant.

16. A method for preventing graft vs. host disease (GvHD) while retaining graft vs. tumor (GvT) activity, comprising the steps of:
(a) providing a sample comprising a cell population, said cell population comprises HSPC and immune cells;
(b) contacting said cell population with an apoptosis-inducing ligand for 2-16 hours in the device of claim 1;
(c) retrieving the cells of step (b); and
(d) transplanting the cells of step (c),
thereby preventing graft vs. host disease (GvHD) while retaining graft vs. tumor (GvT) activity.

* * * * *